US012599338B2

(12) United States Patent
Balkovec et al.

(10) Patent No.: US 12,599,338 B2
(45) Date of Patent: Apr. 14, 2026

(54) DEFLECTABLE ELONGATED GUIDEWIRE ASSEMBLY

(71) Applicant: Boston Scientific Medical Device Limited, Ballybrit (IE)

(72) Inventors: Christian Balkovec, Burlington (CA); Matthew DiCicco, Toronto (CA); Eduardo Moriyama, Richmond (CA); Gareth Davies, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 525 days.

(21) Appl. No.: 17/928,947

(22) PCT Filed: May 25, 2021

(86) PCT No.: PCT/IB2021/054539
§ 371 (c)(1),
(2) Date: Dec. 1, 2022

(87) PCT Pub. No.: WO2021/255553
PCT Pub. Date: Dec. 23, 2021

(65) Prior Publication Data
US 2023/0309929 A1      Oct. 5, 2023

Related U.S. Application Data

(60) Provisional application No. 63/051,080, filed on Jul. 13, 2020, provisional application No. 63/041,319, filed on Jun. 19, 2020.

(51) Int. Cl.
*A61B 5/00*      (2006.01)
*A61B 90/00*      (2016.01)
*A61M 25/09*      (2006.01)

(52) U.S. Cl.
CPC .......... *A61B 5/6851* (2013.01); *A61B 5/6885* (2013.01); *A61B 5/7455* (2013.01);
(Continued)

(58) Field of Classification Search
CPC .... A61B 5/6851; A61B 5/6885; A61B 5/7455
See application file for complete search history.

(56) References Cited

U.S. PATENT DOCUMENTS 5,147,317 A      9/1992   Shank et al.
5,643,251 A      7/1997   Hillsman et al.
(Continued)

FOREIGN PATENT DOCUMENTS

EP      0597195 A2      5/1994
EP      2922593 B1      4/2020
(Continued)

OTHER PUBLICATIONS

International Search Report and Written Opinion received for PCT Patent Application No. PCT/IB2021/054539, mailed on Aug. 26, 2021, 11 pages.

*Primary Examiner* — Daniel L Cerioni
(74) *Attorney, Agent, or Firm* — Nelson Mullins Riley & Scarborough LLP

(57)      ABSTRACT

An elongated guidewire assembly has a distal segment configured to be selectively maneuvered, along an elongated Introducer assembly. The distal segment is configured to selectively transmit a tenting force from the elongated guidewire assembly to the first biological wall after the distal segment has contacted, at least in part, the first biological wall and the distal segment has been selectively protracted away from the distal introducer assembly.

11 Claims, 20 Drawing Sheets

(52) U.S. Cl.
  CPC ................ *A61B 2090/3966* (2016.02); *A61M 2025/09066* (2013.01); *A61M 2025/09175* (2013.01)

(56) References Cited

U.S. PATENT DOCUMENTS

| | | | |
|---|---|---|---|
| 2002/0022830 A1 | 2/2002 | Sharkey et al. | |
| 2002/0123749 A1* | 9/2002 | Jain .................... | A61B 18/1492 |
| | | | 606/41 |
| 2004/0106897 A1 | 6/2004 | Thompson et al. | |
| 2006/0189896 A1 | 8/2006 | Davis et al. | |
| 2013/0046305 A1* | 2/2013 | Davies ............... | A61B 18/1492 |
| | | | 606/45 |
| 2015/0290432 A1 | 10/2015 | Mathews et al. | |
| 2016/0058504 A1* | 3/2016 | Davies ................ | A61B 8/4494 |
| | | | 600/424 |
| 2016/0175009 A1* | 6/2016 | Davies ............... | A61B 17/3478 |
| | | | 606/191 |
| 2019/0167351 A1 | 6/2019 | Salazar et al. | |
| 2020/0305970 A1* | 10/2020 | Ben-Haim ........... | A61B 5/6852 |
| 2021/0068892 A1 | 3/2021 | Urbanski et al. | |
| 2021/0145365 A1* | 5/2021 | Howard ............. | A61B 18/1492 |

FOREIGN PATENT DOCUMENTS

| | | | |
|---|---|---|---|
| WO | 2015/019132 A1 | 2/2015 | |
| WO | 2019/215621 A1 | 11/2019 | |

* cited by examiner

DEFLECTABLE ELONGATED GUIDEWIRE ASSEMBLY

TECHNICAL FIELD

This document relates to the technical field of (and is not limited to): (A) a synergistic combination of an elongated introducer assembly and a deflectable elongated guidewire assembly (and method thereof); and/or (B) a deflectable elongated guidewire assembly for use with an elongated introducer assembly 100 (and method thereof); and/or (C) an elongated introducer assembly configured for use with a deflectable elongated guidewire assembly (and method thereof).

BACKGROUND

Known medical devices are configured to facilitate a medical procedure and help healthcare providers diagnose and/or treat medical conditions of sick patients.

SUMMARY

It will be appreciated that there exists a need to mitigate (at least in part) at least one problem associated with existing (known) guidewires. After much study of, and experimentation with, the existing (known) guidewires, an understanding (at least in part) of the problem and its solution have been identified (at least in part) and are articulated (at least in part) as follows:

Gaining epicardial access involves piercing the thin pericardial layer (also called the pericardium layer) that surrounds the myocardium layer of the heart (without puncturing the myocardium layer). The pericardium layer (also called the pericardial sac) is an outer layer made from connective tissue and holds the heart and the roots of the great vessels (in place in the chest cavity). The myocardium layer is the thick, middle layer of the heart and is composed of cardiac muscle. It is known that mechanical needles may be used to puncture the pericardium layer, where the user might control the input force (also called a tenting force) to be applied to the pericardium layer (via the needle) while attempting, as best as possible, to avoid inadvertently damaging and/or puncturing the underlying myocardium layer (of the heart).

Known epicardial puncture methods involve aiming a relatively stiff (or supported) puncture device directly at the pericardium layer, which is also directly in the pathway toward the underlying myocardium layer. This technique may (unfortunately) result in a higher sensitivity to the force (tenting force) to be applied to the pericardium layer (and underlying myocardium layer) in response to a relatively small change in the displacement (movement) of the puncture device. As a result, it may be very easy to inadvertently apply too much tenting force to the pericardium layer (via the puncture device), and then inadvertently puncture (damage) the myocardium layer. Application of radiofrequency energy (by emission from an electrode and/or a radiofrequency device) for forming a puncture hole through the pericardium layer may be an overall safer and more efficacious method compared to using mechanical needles and/or guidewires. A blunt electrode of the radiofrequency needle may be positioned at the pericardium layer, and the blunt electrode is activated to emit radiofrequency energy, and the surrounding tissue may become vaporized (for the formation of the puncture hole extending through the pericardium layer).

After activation of the blunt electrode for only a fraction of a second (for the formation of the puncture hole), the radiofrequency energy is (quickly) deactivated, and this arrangement may reduce the risk of inadvertent puncture of the myocardium layer. Known methods are similar as outlined above, where a stiff (or supported) radiofrequency puncture device is directed at the pericardium layer. The user may apply the tenting force to the tissue (thereby forming a tent in the tissue). The tenting force might be applied with the radiofrequency electrode placed in an inactive state. When radiofrequency energy is activated (emitted), the tented tissue will become vaporized until the applied force (the tenting force) is reduced to zero as a result of the formation of the puncture hole. With this known method, however, it may be easy to over-tent the tissue prior to activation of the radiofrequency energy given the high sensitivity of the tenting force in response to the placement, movement and/or displacement of the puncture device. Given the proximity of the myocardium layer and the pericardium layer, it remains relatively easy to inadvertently puncture the myocardium layer using this known method and/or known devices.

FIG. 1A, FIG. 1B and FIG. 1C depict side views of a known radiofrequency-puncture method with associated known devices. FIG. 1A depicts a starting point in which the known distal puncture device 292 (such as an electrode) of a known guidewire assembly 290 (see FIG. 2A) is positioned against the pericardium layer 911. FIG. 1B depicts a tenting force 700 applied to the pericardium layer 911 (tissue) from the known guidewire assembly 290. The pericardium layer 911 is forced to take on the shape of a tent in response to the application of the tenting force 700 to the pericardium layer 911. The radiofrequency energy is activated and emitted from the known distal puncture device 292 so that the known distal puncture device 292 (blunt electrode) emits radiofrequency energy toward the zone of the tented pericardium layer 911. FIG. 1C depicts the pericardium layer 911 sliding along and over the known guidewire assembly 290, back to approximately the starting point, as depicted in FIG. 1A. Referring to the embodiments as depicted in FIG. 1A to FIG. 1C, the known guidewire assembly 290 with the known distal puncture device 292 (radiofrequency emitting device), in use, tents the pericardium layer 911 (tissue or biological wall) by applying the tenting force 700 to the tissue. Because the known distal puncture device 292 (radiofrequency emitting device) is blunt, the known distal puncture device 292 does not mechanically puncture the tissue. When radiofrequency energy is applied by, or emitted from, the known distal puncture device 292, the tented pericardium layer 911 is vaporized until the applied tenting force 700 (that is, applied to the pericardium layer 911) returns to zero (as depicted in FIG. 1A), and the pericardium layer 911 may then relax.

FIG. 2A and FIG. 2B depict a close-up cross-sectional side view (FIG. 2A) and a schematic view (FIG. 2B) of the known pericardium puncture using a known puncture device.

Referring to FIG. 2A, the distal tip of the distal puncture device 292 (of the known guidewire assembly 290) is directed (along a known introducer assembly 190) toward the pericardium layer 911 of the heart 940. The pericardium space 931 is located between the pericardium layer 911 and myocardium layer 921. This case presents a higher sensitivity for the tenting force 700 when applied to the pericardium layer 911 in response to small changes in displacement of the known guidewire assembly 290 and/or the known introducer assembly 190.

Referring to FIG. 2B, the vertical axis 390 represents the amount of the tenting force 700. The horizontal axis 392 represents the amount of displacement of the known introducer assembly 190 and/or the known guidewire assembly 290. The first zone 394 indicates a relatively safer range of the tenting force 700 that might be applied to the pericardium layer 911 without damaging the myocardium layer 921 when the known distal puncture device 292 is activated. The purpose of puncturing through the pericardium layer 911 is to gain access to the pericardium space 931, and so that a treatment device may then gain access to the myocardium layer 921 and/or epicardium layer via the puncture hole extending though the pericardium layer 911. It will be appreciated that the epicardium layer is a thin layer on top of the myocardium layer. Epicardial access can also be referred to as an alternative to gaining access to the pericardium space. The second zone 396 indicates a range of a relatively potentially dangerous range of the tenting force 700 that, when applied to the pericardium layer 911, the myocardium layer 921 might become, unfortunately, damaged when the distal puncture device 292 is activated. It is clear that using this known method and/or known devices might present difficulties to achieve a condition in which the tenting force 700 to be applied to the pericardium layer 911 may be sufficient to achieve only pericardium puncture and avoidance of puncturing of (damage to) the myocardium layer 921. It will be appreciated that mere contact or proximity of the electrode to the pericardium layer 911 might vaporize a puncture hole through the pericardium layer 911 by using radiofrequency energy. Epicardial access may be extremely sensitive as puncture of a thin layer of the pericardium layer 911 without damage to the underlying myocardium layer 921 may be desired. What may be desired is a method and/or devices for application of an ideal amount of the tenting force 700 to the pericardium layer 911 in order to achieve only pericardium puncture and avoidance of puncturing (damaging) the myocardium layer 921.

To mitigate, at least in part, at least one problem associated with the existing technology, there is provided (in accordance with a broad aspect) an apparatus. The apparatus is for use with a first biological wall and a second biological wall (the second biological wall being positioned proximate to the first biological wall) of a patient, and an elongated introducer assembly having a distal introducer exit portal. The distal introducer exit portal is configured to be selectively maneuvered and positioned proximate to the first biological wall. The apparatus includes and is not limited to (comprises) an elongated guidewire assembly having a distal segment terminated at a distal puncture device configured to be selectively maneuvered, along the elongated introducer assembly. The distal segment has a distal length configured to contact, at least in part, the first outer surface of the first biological wall; this is done in response to selective protracted movement of the distal segment and the distal puncture device away from the distal introducer exit portal after the distal introducer exit portal has been maneuvered proximate to the first outer surface of the first biological wall. The distal segment is configured to transmit a tenting force from the elongated guidewire assembly to the first biological wall in response to application of the tenting force along, at least in part, the elongated guidewire assembly after the distal length of the distal segment has contacted, at least in part, the first outer surface of the first biological wall (without damaging the second biological wall being positioned proximate to the first biological wall).

To mitigate, at least in part, at least one problem associated with the existing technology, there is provided (in accordance with a broad aspect) an apparatus. The apparatus is for use with a first biological wall and a second biological wall (the second biological wall being positioned proximate to the first biological wall) of a patient. The apparatus includes and is not limited to (comprises) an elongated introducer assembly having a distal introducer exit portal configured to be selectively maneuvered and positioned proximate to the first biological wall. The elongated guidewire assembly has a distal segment terminated at a distal puncture device configured to be selectively maneuvered along the elongated introducer assembly. The distal segment has a distal length configured to contact, at least in part, the first outer surface of the first biological wall; this is done in response to selective protracted movement of the distal segment and the distal puncture device away from the distal introducer exit portal after the distal introducer exit portal has been maneuvered proximate to the first outer surface of the first biological wall. The distal segment is configured to transmit a tenting force from the elongated guidewire assembly to the first biological wall in response to application of the tenting force along, at least in part, the elongated guidewire assembly after the distal length of the distal segment has contacted, at least in part, the first outer surface of the first biological wall (without damaging the second biological wall being positioned proximate to the first biological wall).

To mitigate, at least in part, at least one problem associated with the existing technology, there is provided (in accordance with a broad aspect) a method. The method is for using an elongated guidewire assembly and an elongated introducer assembly with a first biological wall and a second biological wall (the second biological wall being positioned proximate to the first biological wall) of a patient. The method includes and is not limited to (comprises) selectively maneuvering the elongated guidewire assembly having a distal segment terminated at a distal puncture device along the elongated introducer assembly. The method also includes and is not limited to selectively protracting the distal segment and the distal puncture device away from the distal introducer exit portal after the distal introducer exit portal has been maneuvered proximate to the first outer surface of the first biological wall. The method also includes and is not limited to contacting, at least in part, the distal segment (having a distal length) with (against) the first outer surface of the first biological wall after selectively protracting the distal segment and the distal puncture device away from the distal introducer exit portal. The method also includes and is not limited to applying a tenting force along, at least in part, the elongated guidewire assembly after the distal length of the distal segment has contacted, at least in part, the first outer surface of the first biological wall. The method also includes and is not limited to transmitting the tenting force, via the distal segment, from the elongated guidewire assembly to the first biological wall after the tenting force has been applied to the elongated guidewire assembly (without damaging the second biological wall being positioned proximate to the first biological wall).

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter and is not intended to describe each disclosed embodiment or every implementation of the disclosed subject matter. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1A:
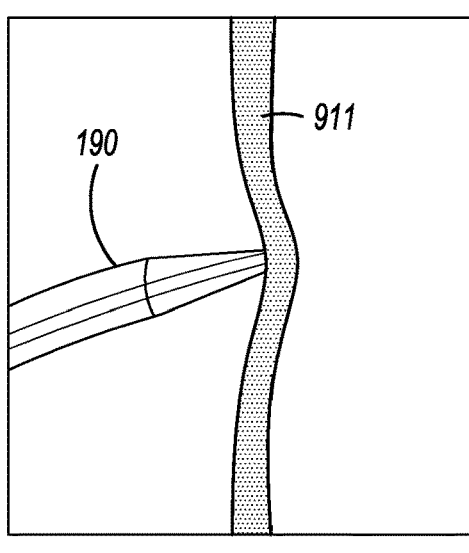
FIG. 1A, FIG. 1B and FIG. 1C depict side views of a known radiofrequency-puncture method associated with known devices.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS

| | |
|---|---|
| elongated introducer assembly 100 | optimal distal portion 206 |
| introducer lumen 102 | elbow portion 209 |
| distal introducer exit portal 104 | axis 300 |
| elongated guidewire assembly 200 | axis 302 |
| distal puncture device 202 | first zone 304 |
| distal length 204 | second zone 306 |
| distal segment 205 | first medical image 401 |
| second medical image 402 | second wire 822 |
| ST-segment elevation 500 | patient 900 |
| electrogram signal 502 | first biological wall 910 |
| tenting force 700 | pericardium layer 911 |
| stretched coil 802 | first outer surface 912 |
| compressed coil 804 | second biological wall 920 |
| distal coil 806 | myocardium layer 921 |
| marker 808 | second outer surface 922 |
| tactile portion 810 | biological space 930 |
| hub 812 | pericardium space 931 |
| proximal visual marker 814 | heart 940 |
| sensor 816 | diaphragm 942 |
| contrast material 818 | liver 944 |
| first wire 821 | |

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise.

It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 3A:
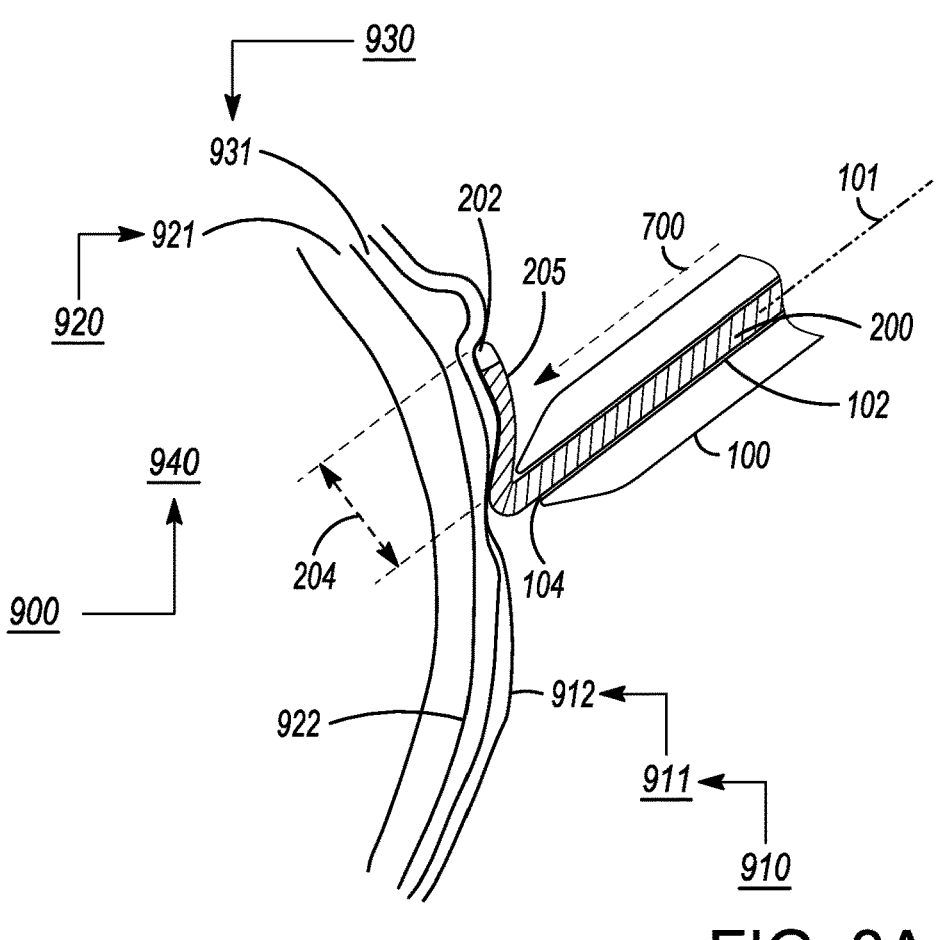
FIG. 3A depicts a cross-sectional view of embodiments of an elongated guidewire assembly.

Referring to the embodiment as depicted in FIG. 3A, a distal length 204 of a distal segment 205 (a distal portion) of the elongated guidewire assembly 200 is moved, and extended (protruded), from a distal introducer exit portal 104 of an introducer assembly 100 (via an introducer lumen 102 extending along the elongated introducer assembly 100). The distal length 204 of the distal segment 205 of the elongated guidewire assembly 200, in use, is moved to contact (at least in part) and rest on (to bear against) the first outer surface 912 of the first biological wall 910 (or the pericardium layer 911 of the heart 940 of the patient 900). A tenting force 700 is received by the distal segment 205 from the elongated guidewire assembly 200, and the distal segment 205 transmits the tenting force 700 from the elongated guidewire assembly 200 to the first outer surface 912. The first outer surface 912 glides over the second outer surface 922, such that the friction between distal segment 205 and first outer surface 912 results in the first outer surface 912 to bunch up in front of the distal puncture device 202 while creating tension in the first outer surface 912 along the length of distal length 204. Once the conditions of tension and bunching up are attained (see FIG. 3B) a puncture can be created (for example, using an RF or mechanical device, such as a flexible wire or equivalent thereof).

Figure 3B:
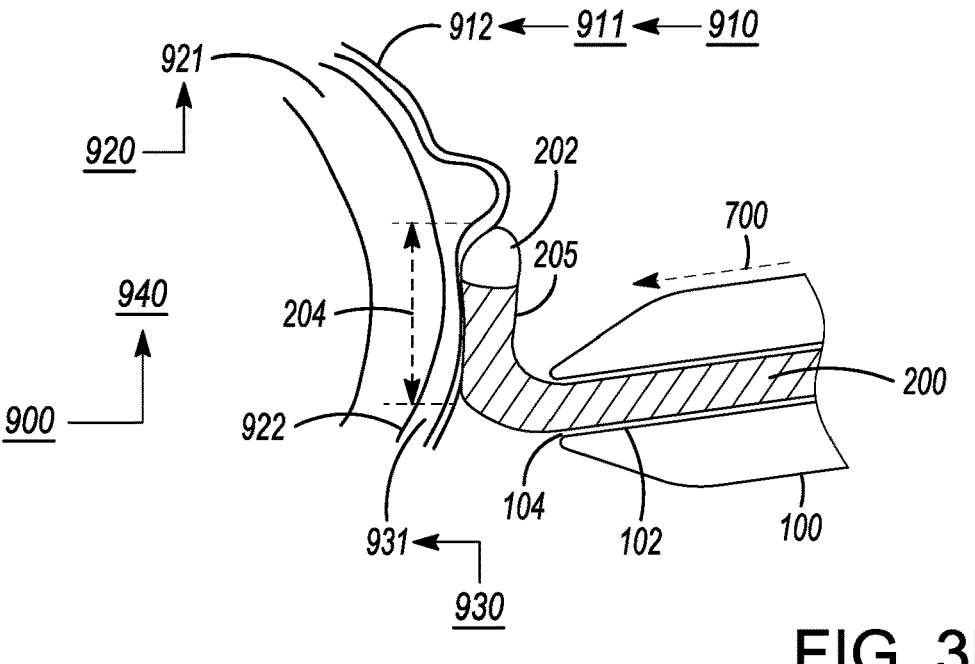
FIG. 3B depicts a closeup of FIG. 3A showing the tissue bunching of the first biological wall of embodiments of an elongated guidewire assembly.

The workflow to obtain the tissue bunching and tension configuration shown in FIG. 3B is as follows: the elongated introducer assembly 100 is positioned proximate to the first biological wall 912; an elongated guidewire assembly 200 is advanced through the introducer lumen 102; the distal puncture device 202 exits the distal introducer exit portal 104 and makes contact with the first biological wall 912; during continued advancement of the elongated guidewire assembly 200 a distal length 204 of the distal segment 205 prolapses over the first biological wall 912 (i.e. distal segment 205 deflects backwards after contacting first biological wall 912 and advances over the surface of first biological wall 912 to arrive at the configuration of FIG. 3A), causing the distal puncture device to be positioned parallel to the second biological wall 922 and bunching a portion of the tissue of the first biological wall 912 in front of the distal puncture device 202 while creating tension in a portion of the tissue of the first biological wall 912 adjacent to the distal length 204 of the distal segment 205. Following this workflow, a puncture is created in the first biological wall 912 via the distal puncture device 202 and the elongated guidewire assembly 200 is advanced into the pericardium space 931 as depicted in FIG. 3E. An RF-based distal puncture device 202 is able to create a puncture in the first biological wall 912 via RF energy while a sharp mechanically-based distal puncture device 202 is able to create a puncture in the first biological wall by protruding from the distal guidewire assembly 200 and then being retracted into the distal guidewire assembly 200 following successful tissue puncture.

Figure 2A:
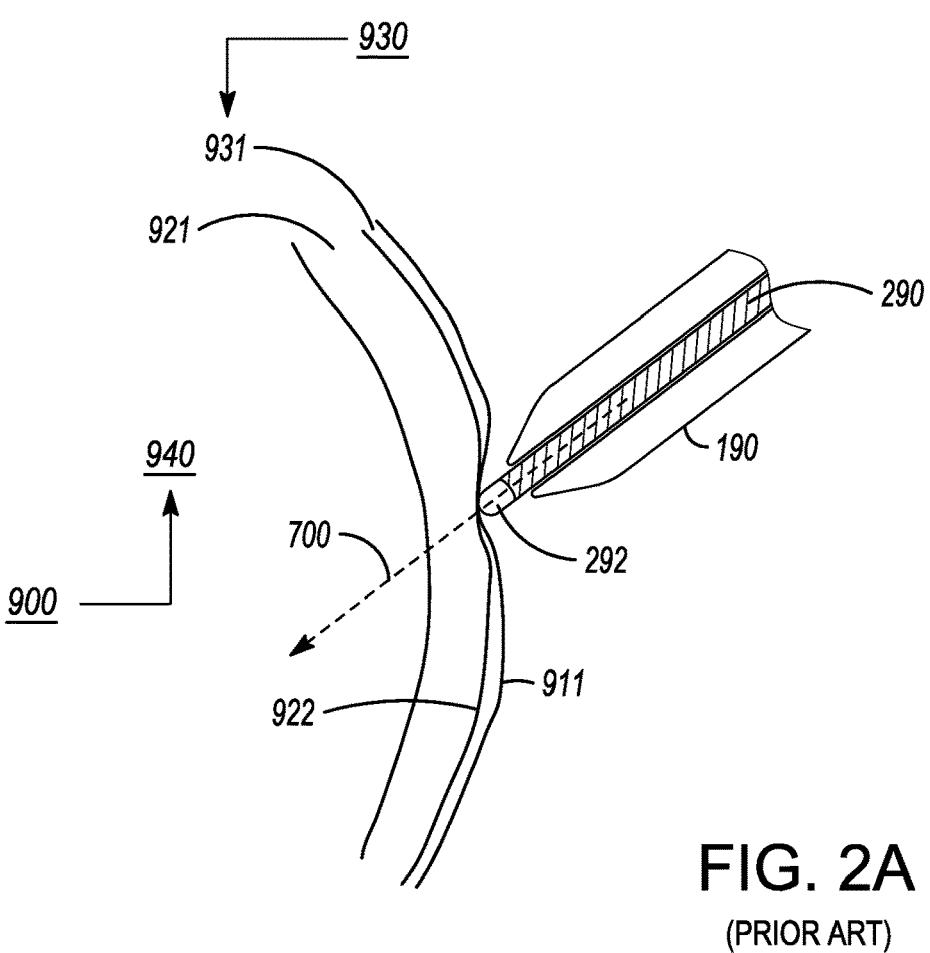
FIG. 2A and FIG. 2B depict a close-up cross-sectional side view (FIG. 2A) and a schematic view (FIG. 2B) of the known pericardium puncture using a known puncture device.
Figure 2B:
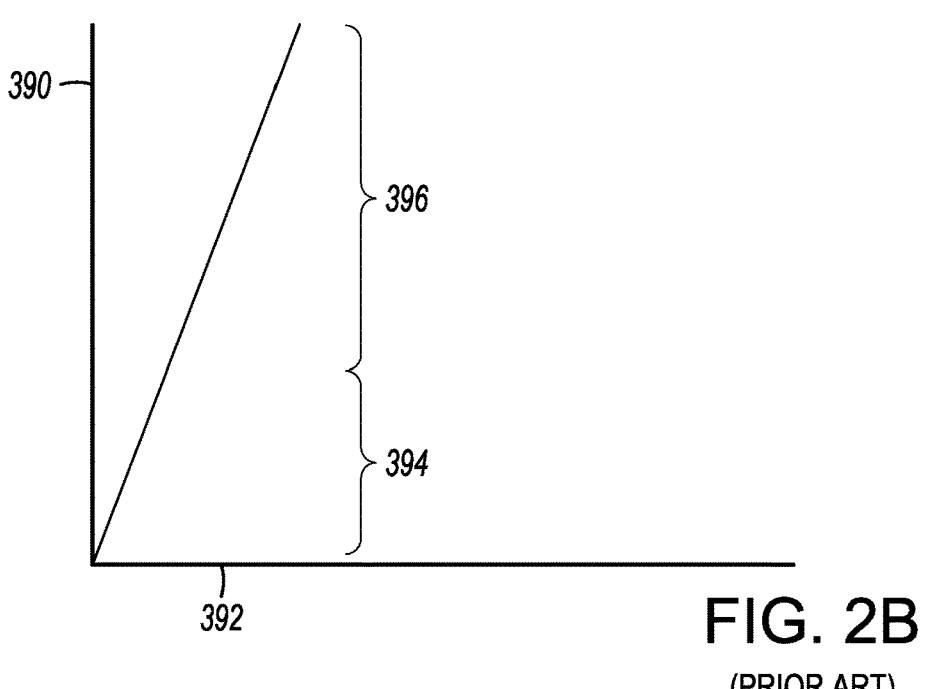
Figure 3C:
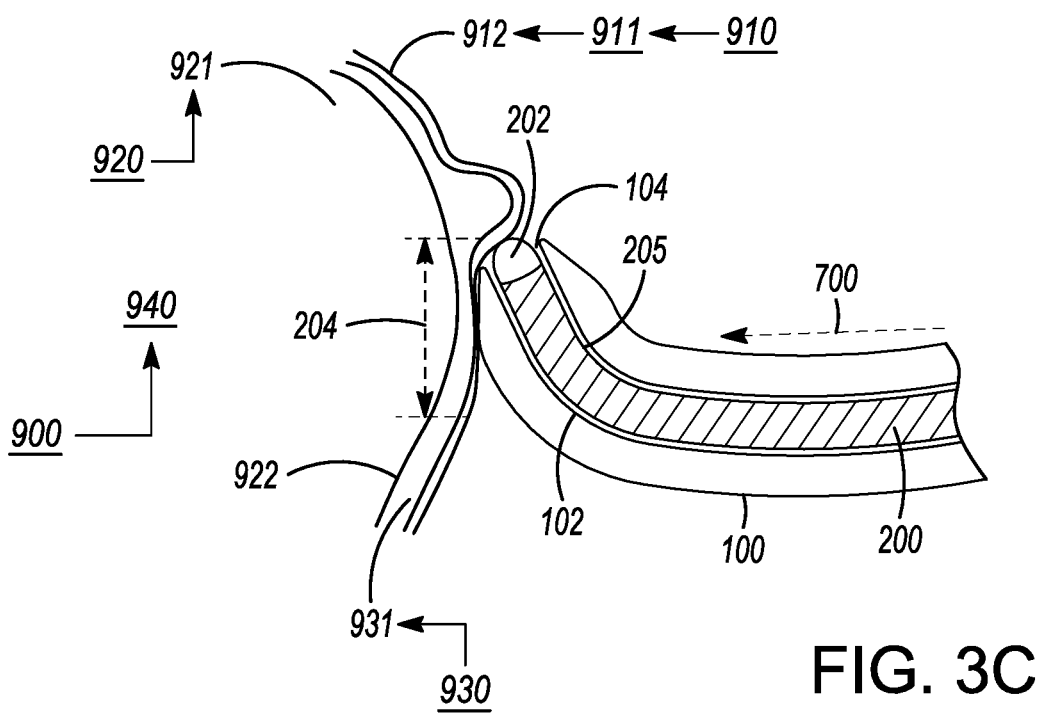
FIG. 3C depicts a cross-sectional view of embodiments of FIG. 3A of an elongated guidewire assembly with a flexible introducer 100 showing the tissue bunching.

The workflow to obtain the tissue bunching and tension configuration shown in FIG. 3C is as follows: a flexible elongated introducer assembly 100 makes contact with the first biological wall 912. A distal length 204 of the distal segment 205 prolapses over the first biological wall, causing the flexible elongated introducer assembly 100 to be positioned parallel to the second biological wall 922 and bunching a portion of the first biological wall in front of the distal introducer exit portal 104 while creating tension in a portion of the tissue of the first biological wall 912 adjacent to the distal length 204 of the distal segment 205. Following this workflow, an elongated guidewire assembly 200 is advanced through the introducer lumen 102. The distal puncture device exits the distal introducer exit portal 104 and is advanced into the first biological wall 912 until puncture of the first biological wall 912 is achieved via the sharp tip of the distal puncture device 202 as depicted in FIG. 3F. The amount of the tenting force 700 to be transmitted from the distal length 204 of the distal segment 205 (of the elongated guidewire assembly 200) to the first biological wall 910 is, advantageously, spread over (dispersed over) a larger portion of the first biological wall 910; in sharp contrast to the embodiment as depicted in FIG. 2A, the tenting force 700 is more focused at, and directed to, a smaller section of the first biological wall 910, and the tenting force 700 is transmitted (entirely) from the known distal puncture device 292 of the known guidewire assembly 290 to the first biological wall 910. Referring back to the embodiment as depicted in FIG. 3A, a lower amount of the tenting force 700 may be applied to the first outer surface 912 (of the first biological wall 910 or the pericardium layer 911) before the distal puncture device 202 (of the elongated guidewire assembly 200) is utilized for the formation of a puncture hole to be extended through the first biological wall 910; advantageously, this arrangement may avoid, at least in part, imparting unwanted damage to the second biological wall 920 (or the myocardium layer 921) as a result of deployment of a relatively lower amount of the tenting force 700 (in comparison to the amount that might be deployed in association with the embodiment of FIG. 2A). The distal puncture device is also redirected away from the second biological wall 922 (as shown in FIG. 3A, FIG. 3B, and FIG. 3C and is in contrast with the known prior art of FIG. 2A) and is no longer positioned perpendicular to the second biological wall 922, but rather, parallel to the second biological wall 922. In this parallel configuration, the distal puncture device 202 is prevented from imparting unwanted damage to the second biological wall 922.

Figure 1B:
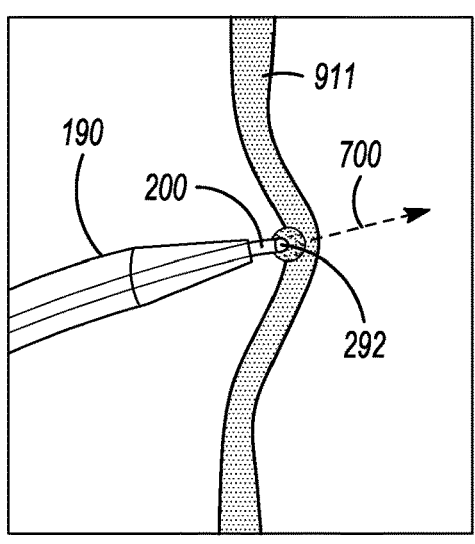
Figure 1C:
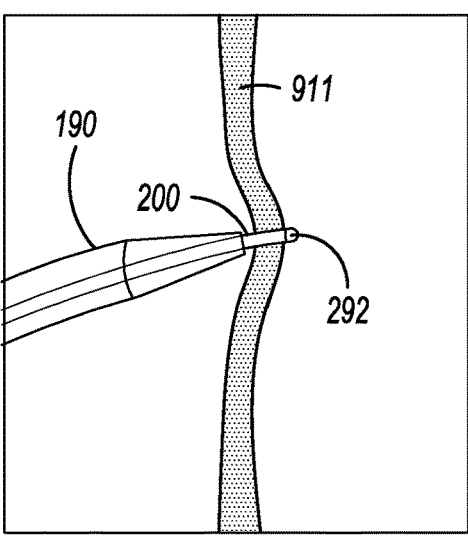

Referring to the embodiment as depicted in FIG. 3A, it will be appreciated that the amount of the tenting force 700 to be transmitted from the distal length 204 of the distal segment 205 (of the elongated guidewire assembly 200) to the first biological wall 910 may be relatively lower in comparison to the amount of the tenting force 700 associated with the embodiment as depicted in FIG. 2A (in FIG. 2A, the tenting force 700 is entirely focused and transmitted from the distal puncture device 202 of the elongated guidewire assembly 200 to the first biological wall 910). The amount of the tenting force 700 (associated with FIG. 3A) may be relatively lower compared to the direct tenting method (as depicted in FIG. 2A and/or FIG. 1B). Advantageously, the amount of the tenting force 700 (associated with FIG. 3A) may be relatively less sensitive to changes in the displacement of the elongated introducer assembly 100.

Referring to the embodiment as depicted in FIG. 3A, it will be appreciated that the direction of the distal puncture device 202 is parallel with the second biological wall 922 (as compared with the perpendicular configuration depicted in FIG. 2A). Advantageously, this parallel configuration prevents the distal puncture device 202 from imparting unwanted damage to the second biological wall 922.

Referring to the embodiment as depicted in FIG. 3B, it will be appreciated that the tissue of the first biological wall 912 is bunched in front of the distal puncture device 202 which is positioned parallel to the second biological wall 922. In this way, the first biological wall 912 can be punctured by the distal puncture device 202 without inadvertent puncture or damage the second biological wall 922.

Further, referring to the embodiment as depicted in FIG. 3C (mechanical puncture), it will be appreciated that the tissue of the first biological wall 912 is bunched in front of the distal introducer exit portal 104 which is positioned parallel to the second biological wall 922. In this way, the first biological wall can be punctured by the distal puncture device 202 reducing or avoiding inadvertent puncture or damage to the second biological wall 922.

Referring to the embodiment as depicted in FIG. 3A, the distal length 204 of the distal segment 205 (of the elongated guidewire assembly 200) is configured to extend from the distal introducer exit portal 104 (of the elongated introducer assembly 100 via the introducer lumen 102).

Figure 20:
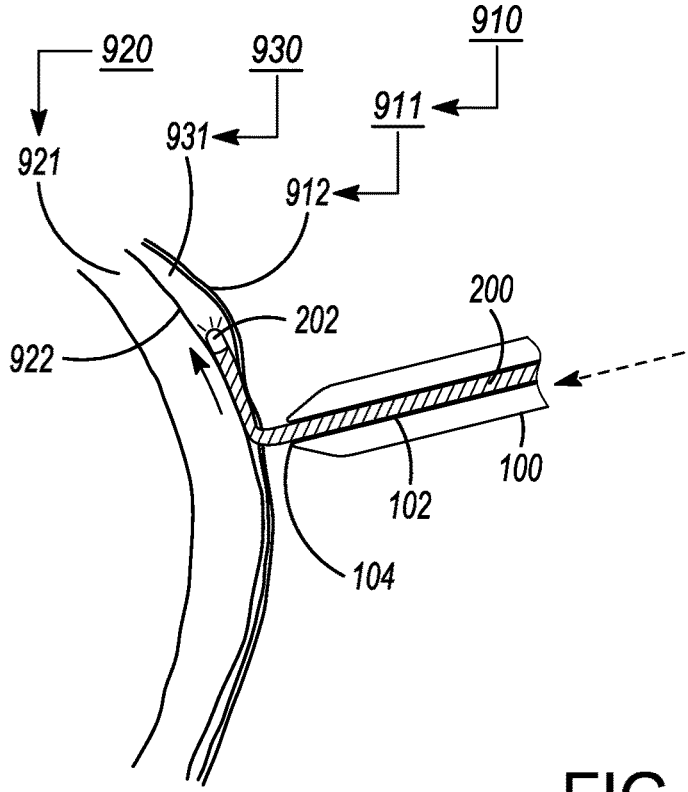

The distal length 204 of the distal segment 205 (also called a distal portion) of the elongated guidewire assembly 200, in use, contacts (rests on, bears against) the first outer surface 912 (of the first biological wall 910 or the pericardium layer 911); advantageously, this arrangement may avoid a potential (unwanted) transfer of (or undue focusing of) the entire amount of the tenting force 700 solely from the distal puncture device 202 toward the first outer surface 912. For this case, the first outer surface 912 may receive a relatively lighter touch (amount) of the tenting force 700 (in comparison to FIG. 2A in which the first outer surface 912 might receive a relatively heavier amount of the tenting force 700). Referring back to FIG. 2A, it will be appreciated that a focused application of the tenting force 700 might likely, and inadvertently, impart unwanted damage to the second outer surface 922 of the second biological wall 920 (or the myocardium layer 921). Referring back to FIG. 3A, advantageously, the amount of the tenting force 700 may be dispersed over a larger portion of the first outer surface 912 (in comparison to that known in the art, as shown in FIG. 2A); in this manner, the present invention (as exemplified in FIGS. 3A to 3D) presents or provides a safer condition for puncturing through the first outer surface 912 (in response to activation of the distal puncture device 202) while the tenting force 700 is applied to the first outer surface 912. In this manner the present embodiment avoids, at least in part, imparting inadvertent damage to the second outer surface 922 (after the first outer surface 912 has been punctured accordingly). In this manner or arrangement, as depicted in FIG. 3A, the tenting force 700 to be applied by the distal length 204 of the distal segment 205 (of the elongated guidewire assembly 200) may be dispersed along the distal length 204 of the distal segment 205 that makes contact with a relatively larger portion of the first outer surface 912 (in comparison to the case as depicted in FIG. 2A). Advantageously, the tenting force 700 to be applied through (via) the distal length 204 of the distal segment 205 of the elongated guidewire assembly 200 (toward the first outer surface 912) remains relatively lower in response to potential changes to the displacement and/or the positioning of the elongated guidewire assembly 200 and/or the elongated introducer assembly 100 relative to the first outer surface 912. This arrangement may give the physician a relatively greater degree of latitude for handling the situation when attempting to impose (impart) the tenting force 700 to the first outer surface 912 (via manipulation of the elongated guidewire assembly 200 and/or the elongated introducer assembly 100); in this manner, a lower degree of influence of mechanical movement to the distal segment 205 of the elongated guidewire assembly 200 may be possible (for the application of the tenting force 700 to the first outer surface 912). After the length of the distal section of the elongated guidewire assembly 200 has been extended from the distal introducer exit portal 104, and the distal length 204 of the distal segment 205 of the elongated guidewire assembly 200 has contacted the first outer surface 912, the tenting force 700 may be applied from the distal length 204 of the distal segment 205 toward the first outer surface 912. While the tenting force 700 is maintained against the first outer surface 912, the distal puncture device 202 (of the elongated guidewire assembly 200) may be utilized (activated) for formation of a puncture hole to be extended through the first outer surface 912 (preferably without imparting unwanted damage to the second biological wall 920 or the myocardium layer 921). It will be appreciated that FIG. 20 depicts the distal puncture device 202 utilized for forming the puncture hole to be extended through the first outer surface 912.

Figure 3D:
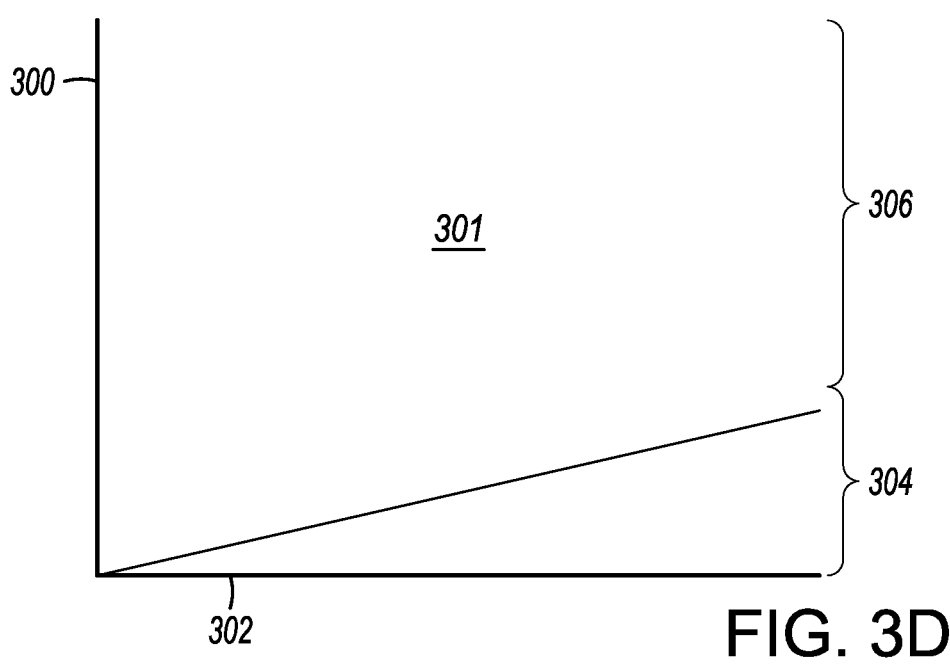
FIG. 3D depicts a schematic view of embodiments of an elongated guidewire assembly.
Figure 3E:
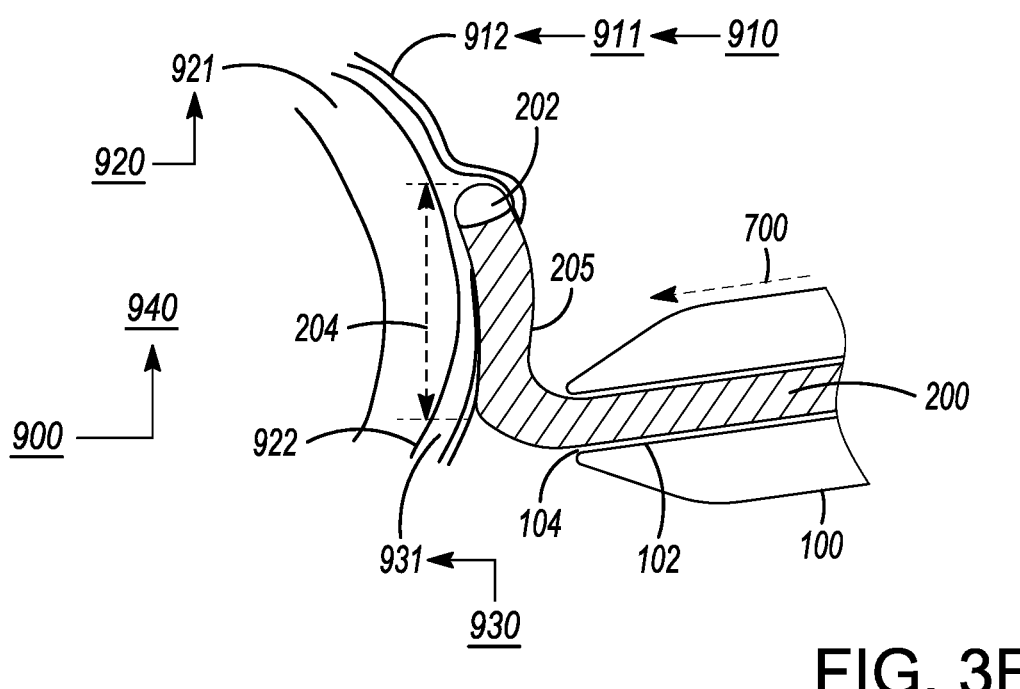
FIG. 3E depicts a cross-sectional view of embodiments of an elongated guidewire assembly after puncture of the first biological wall shown in FIG. 3B.
Figure 3F:
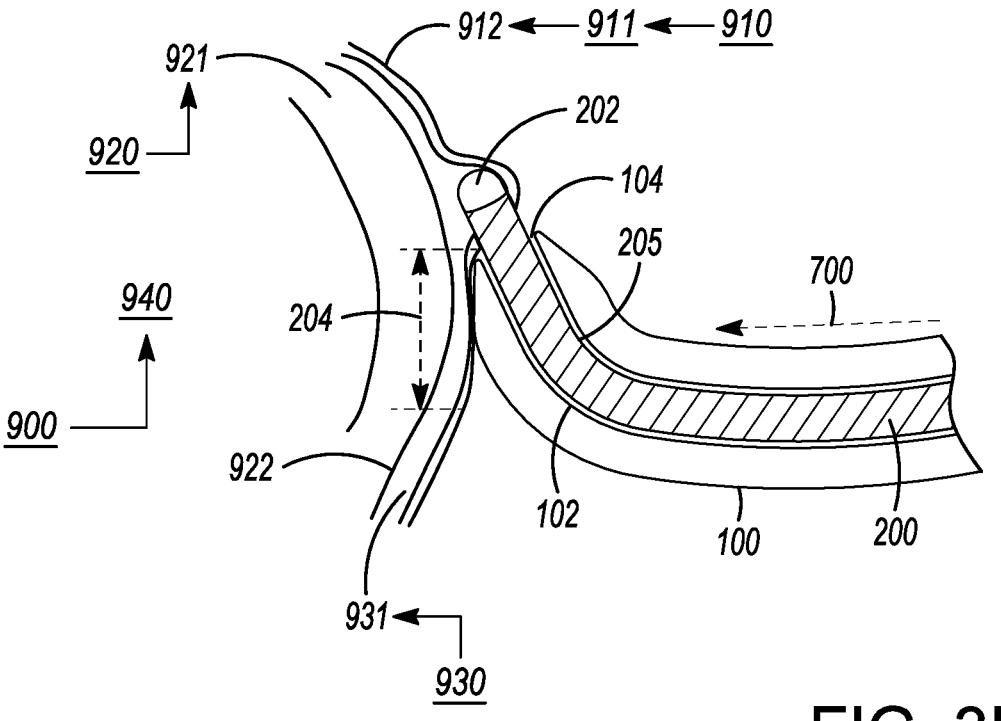
FIG. 3F depicts a cross-sectional view of embodiments of an elongated guidewire assembly after puncture of the first biological wall shown in FIG. 3C.

Referring to the embodiment as depicted in FIG. 3D, a graph 301 is applicable for the embodiment as depicted in FIGS. 3A, 3B and 3C. The axis 300 represents the amount of the tenting force 700. The axis 302 represents the amount of displacement of the elongated introducer assembly 100 and/or the elongated guidewire assembly 200. The first zone 304 indicates a range of a relatively safer amount of the tenting force 700 that might be applied to the first biological wall 910 (or the pericardium layer 911) without damaging the second biological wall 920 (or the myocardium layer 921). The second zone 306 indicates a range of a relatively potentially dangerous amount of the tenting force 700 that, if applied to the first biological wall 910 (or the pericardium layer 911), the second biological wall 920 (or the myocardium layer 921) might become, unfortunately, damaged when the distal puncture device 202 is activated.

Referring to the embodiment as depicted in FIG. 3A, there is provided a procedure (method) including (and not limited to) of puncturing the first biological wall 910 (or the pericardium layer 911). The method includes the following steps: step (1), step (2), step (3) and step (4). Step (1) is depicted in (associated with) FIG. 15; step (2) is depicted in (associated with) FIG. 16; step (3) is depicted in (associated with) FIG. 17 and FIG. 18; and step (4) is depicted in (associated with) FIG. 19 and FIG. 20. Step (1) includes percutaneous delivery of the elongated guidewire assembly 200 to the first biological wall 910 (or the first outer surface 912 of the pericardium layer 911 of the heart 940) via the elongated introducer assembly 100.

Step (2) includes protrusion of the elongated guidewire assembly 200 from the distal introducer exit portal 104 of the elongated introducer assembly 100 (via the introducer lumen 102). Step (3) includes positioning the elongated guidewire assembly 200 so that the distal puncture device 202 (of the elongated guidewire assembly 200) to extend (or to protrude) toward, and become positioned in, an optimal contact relationship with the first outer surface 912 of the first biological wall 910 (or the pericardium layer 911). Step (4) includes utilizing the distal puncture device 202 of the elongated guidewire assembly 200 to puncture through the first outer surface 912 (after application of the tenting force 700 is applied from the length of the distal portion of the elongated guidewire assembly 200 to the first outer surface 912 (without imparting damage to the second biological wall 920 or the myocardium layer 921). It will be appreciated that for step (2) and step (3), various devices and/or techniques may be utilized to assist in obtaining optimal extension (protrusion) of the distal length 204 of the distal segment 205 of the elongated guidewire assembly 200 (from the elongated introducer assembly 100) while, preferably, maintaining the distal length 204 of the distal segment 205 and the distal puncture device 202 in a contact arrangement (relationship) with the first outer surface 912 (prior to utilization of the distal puncture device 202 for formation of the puncture hole to be extended through the first outer surface 912).

Referring to the embodiment as depicted in FIG. 3A, it will be appreciated that the embodiment of FIG. 3A may be utilized for (and is not limited to) obtaining access to the pericardium space 931 of the heart 940, and may be applicable for any type of the biological space 930 positioned between the first biological wall 910 and the second biological wall 920.

Referring to the embodiment as depicted in FIG. 3A, the options for step (1) may include the following options: step (1) option (A) (see FIG. 4A and FIG. 4B) includes usage of electroanatomic mapping (EAM) for positioning assessment; step (1) option (B) (see FIG. 5A and FIG. 5B) includes usage of an electrogram system (EGM) for positioning assessment; and step (1) option (C) (see FIG. 6A and FIG. 6B) includes usage of a tip that may be stiff or floppy (use of the distal puncture device 202 or other accessory device may add stiffness).

Referring to the embodiment as depicted in FIG. 3A, the options for step (2) may include the following options: step (2) option (A)) (see FIG. 7A and FIG. 7B) includes usage of a radiopaque marker (also called an RO marker), a stretched coil and/or a compressed coil (areas of tight and/or loose coil windings) for detection of protrusion length of the elongated guidewire assembly 200. At least one radiopaque marker 808C may also be embedded within the elongated introducer assembly at its distal end (see FIG. 7G). When viewed by a medical imaging system, a user is then able to align the radiopaque marker on the elongated introducer assembly 100 between the two radiopaque markers (808A and 808B) on the elongated guidewire assembly 200 to ensure an optimal length 204 of the distal segment 205 of the elongated guidewire assembly 200 is prolapsing for an optimal application of tenting force to the first biological wall 912; step (2) option (B) (see FIG. 8A, FIG. 8B and FIG. 8C) includes distal and/or proximal tactile markers for detection of protrusion length of the elongated guidewire assembly 200; step (2) option (C) (see FIG. 9) includes a proximal visual marker configured to provide a visual indication for detection of protrusion length of the elongated guidewire assembly 200; and step (2) option (D) (see FIG. 10) includes capacitive sensing for detection of protrusion length of the elongated guidewire assembly 200. The variations for step (2) option (A) may include the following variations: variation (A) includes usage of stretched/spaced coil (areas of tight and loose winding); variation (B) includes coil on the distal section (of the elongated guidewire assembly 200) to be protruded; and variation (C) includes usage of spaced solid markers for depth measurements.

Referring to the embodiment as depicted in FIG. 3A, the options for step (3) may include the following options: step (3) option (A) (see FIG. 11A and FIG. 11B) includes the distal puncture device 202 (of the elongated guidewire assembly 200) in sync with cardiac motion; step (3) option (B) (not depicted) includes sensing of the tenting force at the distal tip; step (3) option (C) (not depicted) includes setting protruded section stiffness (may not exceed critical myocardium puncture threshold); step (3) option (D) (see FIG. 12A and FIG. 12B) includes EAM to visualize contact; step (3) option (E) (not depicted) includes EGM to confirm contact; step (3) option (F) (see FIG. 13) includes injection of a contrast material; step (3) option (G) (see FIG. 14) includes electrical contacts for making and breaking a circuit to indicate when it might be acceptable or unacceptable to apply the tenting force (if too high, the circuit is broken, etc.); and step (3) option (H) (not depicted) includes the distal puncture device positioned at a region where cardiac motion perpendicular to the elongated introducer assembly 100 is minimized.

Referring to the embodiment as depicted in FIG. 3A, the options for step (4) may include the following options: step (4) option (A) (not depicted) includes activation of radiofrequency energy only for the time it takes to vaporize the first biological wall 910 (or the pericardium layer 911) (to optimize the time for activation of the radiofrequency energy to be applied); step (4) option (B) includes activation of the radiofrequency energy only for less than about 0.5 seconds; and step (4) option (C) (not depicted) includes deactivation of the radiofrequency energy when an impedance change is detected (when the distal portion of the elongated guidewire assembly 200 has punctured and entered into the biological space 930 or the pericardium space 931).

Referring to the embodiment as depicted in FIG. 3A, there is depicted an apparatus for use with the first biological wall 910 and the second biological wall 920 (the second biological wall 920 being positioned proximate to the first biological wall 910) of the patient 900, and the elongated introducer assembly 100 having the distal introducer exit portal 104 is configured to be selectively maneuvered and positioned proximate to the first biological wall 910. The apparatus includes and is not limited to an elongated guidewire assembly 200 having a distal segment 205 terminated at a distal puncture device 202 configured to be selectively maneuvered along the elongated introducer assembly 100. This is done, preferably, in such a way that the distal puncture device 202 is positioned proximate to the first biological wall 910 after the distal introducer exit portal 104 has been selectively maneuvered and positioned proximate to the first outer surface 912 of the first biological wall 910. The distal segment 205 has a distal length 204 configured to contact, at least in part, the first outer surface 912 of the first biological wall 910 in response to selective protracted movement of the distal segment 205 and the distal puncture device 202 away from the distal introducer exit portal 104 after the distal introducer exit portal 104 has been maneuvered proximate to the first outer surface 912 of the first biological wall 910. The distal segment 205 is configured to transmit a tenting force 700 from the elongated guidewire assembly 200 to the first biological wall 910 in response to application of the tenting force 700 along, at least in part, the elongated guidewire assembly 200 after the distal length 204 of the distal segment 205 has contacted, at least in part, the first outer surface 912 of the first biological wall 910 (without damaging the second biological wall 920 being positioned proximate to the first biological wall 910).

Referring to the embodiment as depicted in FIG. 3A, the distal segment 205 is configured to be deflected away from a longitudinal axis 101 extending through the elongated introducer assembly 100 by the first outer surface 912 of the first biological wall 910 in response to the distal length 204 making contact, at least in part, with the first outer surface 912 of the first biological wall 910 after the elongated guidewire assembly 200 is protracted from the elongated introducer assembly 100 such that further advancement of distal segment 205 will result in distal segment 205 prolapsing over first outer surface 912 to arrive at the configuration of FIG. 3A.

Referring to the embodiment as depicted in FIG. 3A, the distal length 204 of the distal segment 205 is also configured to transmit the tenting force 700 while the distal puncture device 202 is utilized to puncture through the first biological wall 910.

Referring to the embodiment as depicted in FIG. 3A, there is depicted an apparatus for use with the first biological wall 910 of the patient 900, and the elongated introducer assembly 100 configured to be selectively maneuvered and positioned proximate to the first biological wall 910. The apparatus includes (and is not limited to) the elongated guidewire assembly 200 having a distal segment 205 configured to be selectively maneuvered, along the elongated introducer assembly 100. The distal segment 205 is configured to selectively transmit a tenting force 700 from the elongated guidewire assembly 200 to the first biological wall 910 after the distal segment 205 has contacted, at least in part, the first biological wall 910 and the distal segment 205 has been selectively protracted away from the distal introducer exit portal 104 (of the introducer assembly 100).

Referring to the embodiment as depicted in FIG. 3A, there is depicted a method for use with the first biological wall 910 of the patient 900, and the elongated introducer assembly 100 configured to be selectively maneuvered and positioned proximate to the first biological wall 910. The method includes and is not limited to (comprises) selectively maneuvering an elongated guidewire assembly 200 having a distal segment 205 along the elongated introducer assembly 100. The method also includes selectively transmitting a tenting force 700 via the distal segment 205 from the elongated guidewire assembly 200 to the first biological wall 910 after the distal segment 205 has contacted, at least in part, the first biological wall 910 and the distal segment 205 has been selectively protracted away from the distal introducer exit portal 104 (of the distal introducer assembly 100).

Referring to the embodiment as depicted in FIG. 3A, there is depicted a method of using the elongated guidewire assembly 200 and the elongated introducer assembly 100 with the first biological wall 910 and the second biological wall 920 (the second biological wall 920 being positioned proximate to the first biological wall 910) of the patient 900. The method includes and is not limited to selectively maneuvering the elongated guidewire assembly 200 (the elongated guidewire assembly 200 having a distal segment 205 terminated at a distal puncture device 202) along the elongated introducer assembly 100. The method also includes selectively protracting the distal segment 205 and the distal puncture device 202 away from the distal introducer exit portal 104 after the distal introducer exit portal 104 has been maneuvered proximate to the first outer surface 912 of the first biological wall 910. The method also includes contacting, at least in part, the distal segment 205 having a distal length 204 with the first outer surface 912 of the first biological wall 910 after selectively protracting the distal segment 205 and the distal puncture device 202 away from the distal introducer exit portal 104. The method also includes applying a tenting force 700 along, at least in part, the elongated guidewire assembly 200 after the distal length 204 of the distal segment 205 has contacted, at least in part, the first outer surface 912 of the first biological wall 910. The method also includes transmitting the tenting force 700, via the distal segment 205, from the elongated guidewire assembly 200 to the first biological wall 910 after the tenting force 700 has been applied to the elongated guidewire assembly 200 (without damaging the second biological wall 920 being positioned proximate to the first biological wall 910).

Referring to the embodiment as depicted in FIG. 3A, the components or the elongated introducer assembly 100 and/or the elongated guidewire assembly 200 include biocompatible material properties suitable for performance (such as, dielectric strength, thermal performance, electrical insulation, corrosion resistance, water resistance and/or heat resistance), for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment as depicted in FIG. 3A, the elongated guidewire assembly 200 includes a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus applied to the shape-memory material. This is known as the shape memory effect (SME).

Superelasticity (in alloys) may be observed once the shape-memory material is deformed under the presence (an application) of a stimulus force.

Referring to the embodiment as depicted in FIG. 3A, the distal puncture device 202 includes (and is not limited to) a radiofrequency puncture device, such as the BAYLIS (TRADEMARK) POWERWIRE (REGISTERED TRADE-MARK) radiofrequency guidewire manufactured by BAYLIS MEDICAL COMPANY (headquartered in Canada).

In accordance with another embodiment, the distal puncture device 202 includes (and is not limited to) an elongated guidewire having a distal tip section presenting a mechanical cutting portion.

Referring to the embodiment as depicted in FIG. 3A, the elongated guidewire assembly 200 is configured to be inserted into a confined space defined by a living body (the patient). The guidewire assembly 200 includes (preferably) a relatively thin and flexible wire (an elongated flexible shaft) configured to be inserted into a confined or tortuous space (a confined space) defined by the living body. The guidewire assembly 200 is (preferably) impermeable by a bodily fluid located in the confined space defined by the living body.

Figure 4A:
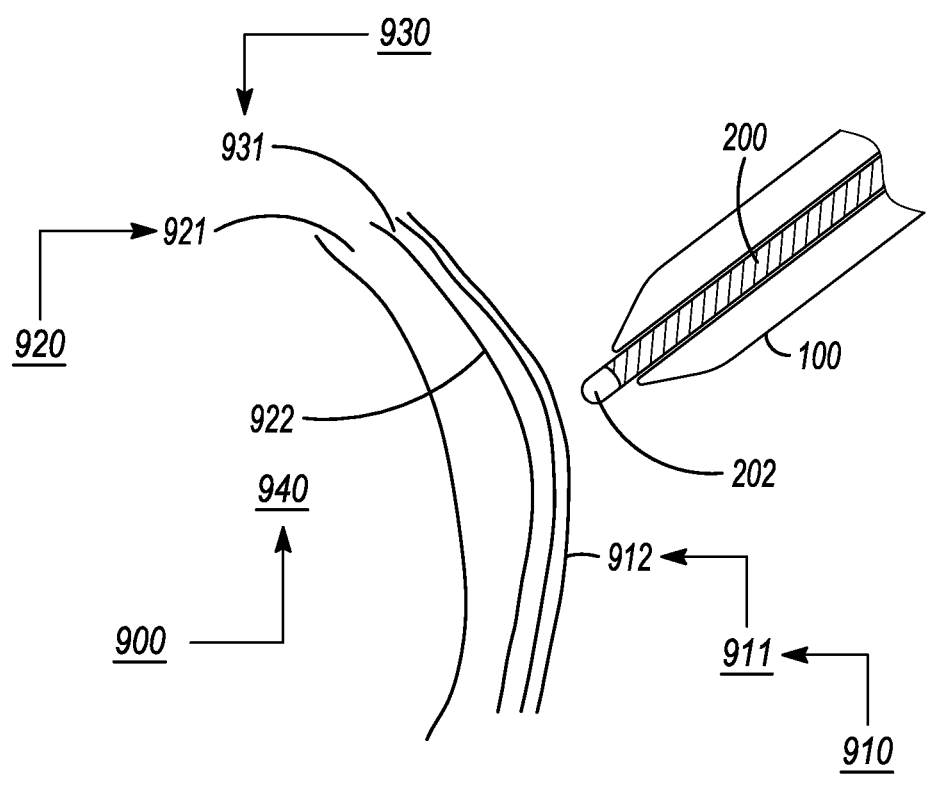
FIG. 4A and FIG. 4B depict a cross-sectional view (FIG. 4A) and a schematic view (FIG. 4B) of embodiments of the elongated guidewire assembly of FIG. 3A.
Figure 4B:
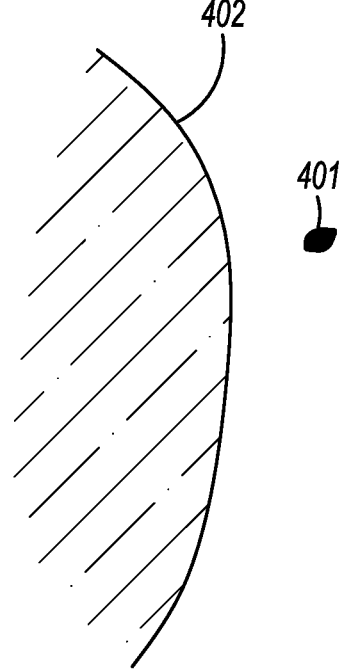

FIG. 4A and FIG. 4B depict a cross-sectional view (FIG. 4A) and a schematic view (FIG. 4B) of embodiments of the elongated guidewire assembly 200 of FIG. 3A. FIG. 4A and FIG. 4B depict the embodiments associated with step (1) option (A).

Referring to the embodiment of FIG. 4A, the distal puncture device 202 (of the elongated guidewire assembly 200) is configured to selectively emit energy (such as radiofrequency energy) for puncturing through the first biological wall 910 (or the pericardium layer 911 of the heart of the patient). The distal puncture device 202 is electrically connected to an electroanatomic mapping system (known and not depicted). Step (1) option (A) includes usage of an electroanatomic mapping system for positioning assessment.

Referring to the embodiment as depicted in FIG. 4B, the medical detection and visualization of a sensing element positioned at the distal tip of the elongated introducer assembly 100 may be performed (computed) by the electroanatomic mapping system (known and not depicted). The electroanatomic mapping system is configured to display (via a display device) a first medical image 401 associated with the distal puncture device 202. The first medical image 401 is rendered on the visual display of the electroanatomic mapping system (EAM) as a live (in situ or in real-time) signal. The electroanatomic mapping system is configured to display a visual map (via a display device known and not depicted) showing the three-dimensional anatomy of the heart (of the patient). The first medical image 401 may be depicted against a second medical image 402 representing a mapped outline (images) of the heart of the patient. The electroanatomic mapping system is configured to track the location of the elongated guidewire assembly 200, provided that the elongated guidewire assembly 200 is electrically connected to the electroanatomic mapping system. The elongated introducer assembly 100 may be configured to facilitate connection with the electroanatomic mapping system, and is configured to indicate the position of the distal portion of the elongated introducer assembly 100, which may allow the user to obtain an optimal positioning of the elongated introducer assembly 100 relative to the heart.

Figure 5A:
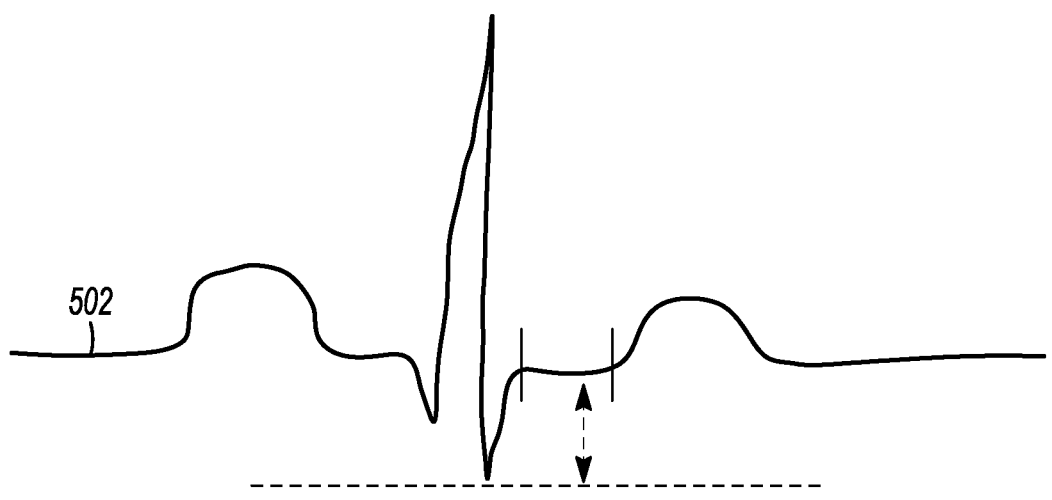
FIG. 5A and FIG. 5B depict schematic views of embodiments of the elongated guidewire assembly of FIG. 3A.
Figure 5B:
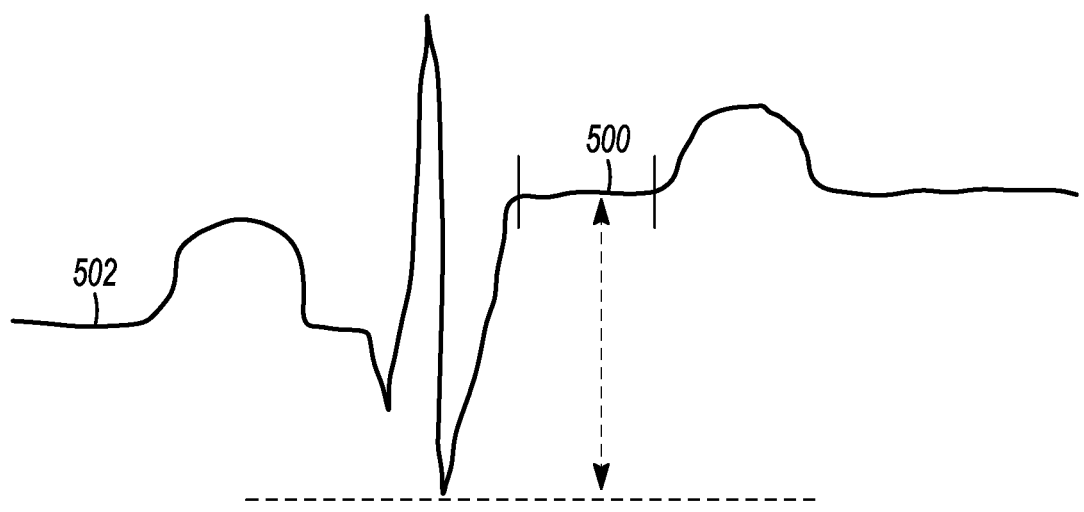

FIG. 5A and FIG. 5B depict schematic views of embodiments of the elongated guidewire assembly 200 of FIG. 3A. FIG. 5A and FIG. 5B depict the embodiments associated with step (1) option (B).

Referring to the embodiments as depicted in FIG. 5A and FIG. 5B, the medical-detection system (known and not depicted) is configured to measure the electrical potential in a tissue. The medical-detection system may include an electrogram system (the electrogram system is configured to provide a tracing of the electrical potentials of biological tissue made by means of electrodes placed directly in the tissue instead of on the surface of the body), an electromyography system (EMG system is configured to provide a recording of the electrical activity of muscle tissue, or its representation as a visual display or audible signal, using electrodes attached to the skin or inserted into the muscle) and any equivalent thereof. The elongated introducer assembly 100 includes a sensor (material) positioned at the tip of the elongated introducer assembly 100. The sensor is configured to conduct electrical signals, and is configured to be electrically connected with the medical-detection system (such as, the electrogram system). The electrogram system may provide feedback to a user about where the elongated introducer assembly 100 is positioned relative to the heart of the patient (based on the information provided by (from) the sensor of the elongated introducer assembly 100). As the elongated introducer assembly 100 is brought closer to the heart, the sensor of the introducer assembly 100 is able to pick up an electrical signal and output that signal to the electrogram system. When the tip of the elongated introducer assembly 100 makes contact with the heart, the tip (of the elongated introducer assembly 100) creates local ischemia in the tissue (of the heart) that changes the electrical signal seen by generating an ST-segment elevation 500 (as depicted in FIG. 5B). Using this, a user is able to tell when the elongated introducer assembly 100 may be ideally positioned. In this manner, a local ischemia created ST-segment elevation 500 may be visualized from the electrogram signal 502.

Figure 6A:
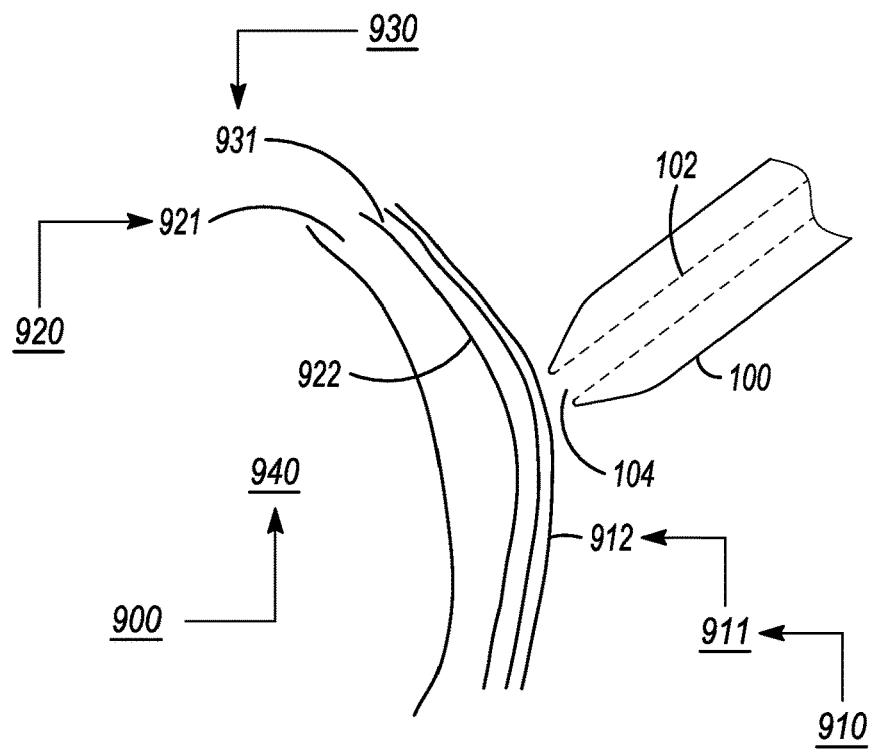
FIG. 6A and FIG. 6B depict cross-sectional views of embodiments of an elongated introducer assembly for use with the elongated guidewire assembly of FIG. 3A.
Figure 6B:
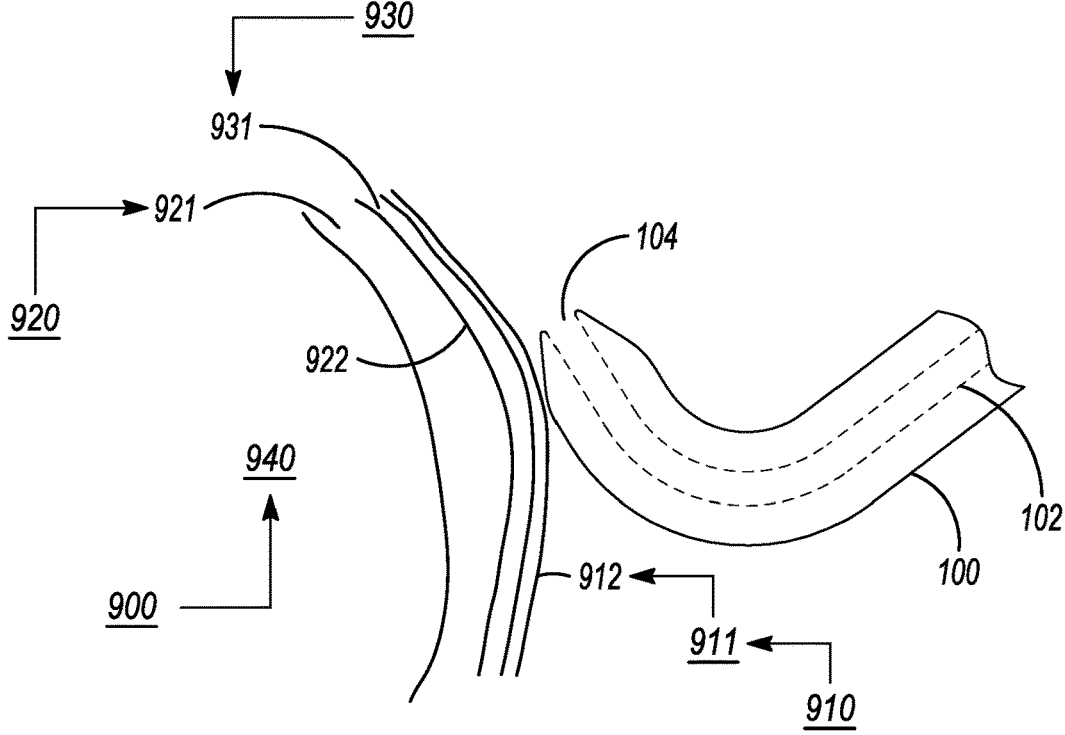

FIG. 6A and FIG. 6B depict cross-sectional views of embodiments of an elongated introducer assembly 100 for use with the elongated guidewire assembly 200 of FIG. 3A. FIG. 6A and FIG. 6B depict the embodiments associated with step (1) option (C).

Referring to the embodiment as depicted in FIG. 6A, the elongated introducer assembly 100 is configured to be relatively floppy (less stiff). The elongated introducer assembly 100 is configured to collapse and/or bend in response to the distal portion of the elongated introducer assembly 100 striking against the outer surface of the first biological wall 910 (or the pericardium layer 911 of the heart of the patient). This case may be more atraumatic during positioning. Usage of a relatively stiffer instance of the distal puncture device 202 or other stiff accessory device may assist in navigation through the tissue and may initially enable a floppy introducer assembly 100 to perform the task. For instance, the elongated introducer assembly 100 may include a tube with a hollow lumen for facilitating delivery of a puncture device. During the initial step, the elongated introducer assembly 100 is delivered through patient tissue. The elongated introducer assembly 100 may be rigid enough to enable this crossing. Once positioned at the heart, however, the elongated introducer assembly 100 does not necessarily need to be as rigid. As a result, a stiffer instance of the distal puncture device 202 may be included, and the distal puncture device 202 may be used when traversing tissue with the elongated introducer assembly 100. The stiffer instance of the distal puncture device 202 may be made of stainless steel and is inserted into the lumen of the elongated introducer assembly 100. The distal puncture device 202 does not move relative to the elongated introducer assembly 100 while in place and may later be removed following tissue traversal. The stiffer instance of the distal puncture device 202 may also function as a conduit for conveyance of EGM signals (for step (1) option (B)) or be connected to the EAM system (for step (1) option (A)) to indicate the position of the distal tip of the introducer to the user while they are initially positioning the elongated introducer assembly 100 at the desired location relative to the heart of the patient.

Figure 7A:
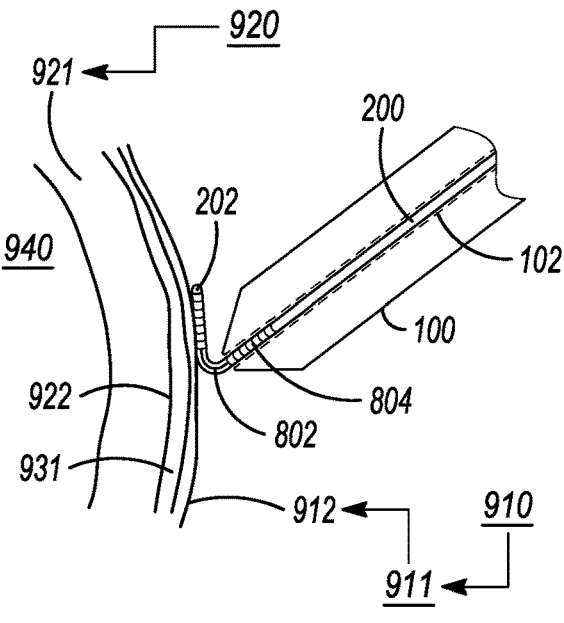
FIG. 7A to FIG. 7G depict cross-sectional views (FIG. 7A, FIG. 7B and FIG. 7E), side views (FIG. 7C, FIG. 7D and FIG. 7F) and a distal end view (FIG. 7G) of embodiments of the elongated guidewire assembly of FIG. 3A.
Figure 7B:
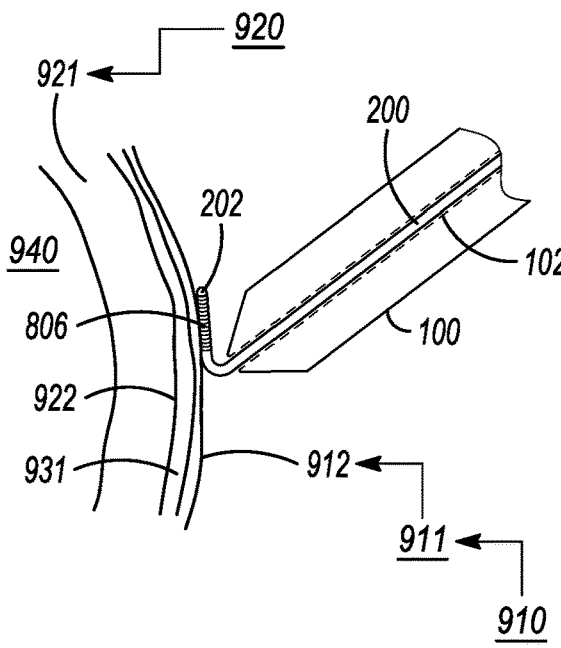

FIG. 7A to FIG. 7F depict cross-sectional views (FIG. 7A, FIG. 7B and FIG. 7E) and side views (FIG. 7C, FIG. 7D and FIG. 7F) of embodiments of the elongated guidewire assembly 200 of FIG. 3A. FIG. 7A and FIG. 7B depict the embodiments associated with step (2) option (A). These options enable the user to know (detect) when the length of the distal segment 205 of the elongated guidewire assembly 200 has been extended (protruded) from the distal end of the elongated introducer assembly 100. The length (of the distal segment 205 of the elongated guidewire assembly 200) is preferably an optimal length, in order to reduce or minimize the amount of the tenting force 700 that might be imparted to the first outer surface 912 of the first biological wall 910 (or the pericardium layer 911).

Referring to the embodiment as depicted in FIG. 7A, the elongated guidewire assembly 200 is (generally) configured to be detectable by a medical imaging system. For instance, the elongated guidewire assembly 200 includes a stretched coil 802 and a compressed coil 804 mounted to the distal segment 205 of the elongated guidewire assembly 200. The stretched coil 802 and the compressed coil 804 are spaced apart from each other. The stretched coil 802 is positioned between the compressed coil 804 and the distal puncture device 202. The stretched coil 802 and the compressed coil 804 are configured to be detectable by a medical imaging system. The stretched coil 802 and the compressed coil 804 are configured to enable the user to visually see, via the medical imaging system (such as, under fluoroscopy or x-ray) when the distal segment 205 (that is, a required or desired length of the distal segment 205 of the elongated guidewire assembly 200) has been protruded from the distal portion of the elongated introducer assembly 100. The stretched coil 802 includes a section of the coil that has a relatively looser winding. The compressed coil 804 includes a section of the coil that has a relatively tighter winding.

Referring to the embodiment as depicted in FIG. 7B, the elongated guidewire assembly 200 includes a distal coil 806 that is positioned at the distal segment 205 of the elongated guidewire assembly 200. The distal coil 806 is positioned proximate to the distal puncture device 202. The distal coil 806 is configured to be detectable by a medical imaging system. The distal coil 806 is configured to enable the user to visually see, via the medical imaging system (such as, under fluoroscopy or x-ray) when the distal segment 205 (that is, a required or desired length of the distal segment 205 of the elongated guidewire assembly 200) has been protruded from the distal portion of the elongated introducer assembly 100.

Figure 7C:
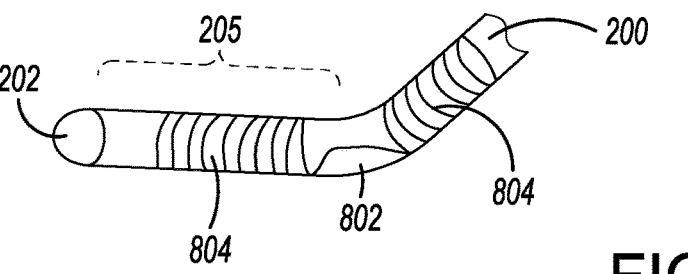

Referring to the embodiment as depicted in FIG. 7C, the elongated guidewire assembly 200 includes a stretched coil 802 positioned between a pair of compressed coils 804. The stretched coil 802 and the pair of compressed coils 804 are mounted to the distal segment 205 of the elongated guidewire assembly 200. One coil of the pair of compressed coils 804 is positioned proximate to the distal puncture device 202. The stretched coil 802 and the pair of compressed coils 804 are configured to be detectable by a medical imaging system. The stretched coil 802 and the pair of compressed coils 804 are configured to enable the user to visually see, via the medical imaging system (such as, under fluoroscopy or x-ray) when the distal segment 205 (that is, a required or desired length of the distal segment 205 of the elongated guidewire assembly 200) has been protruded from the distal portion of the elongated introducer assembly 100.

Figure 7D:
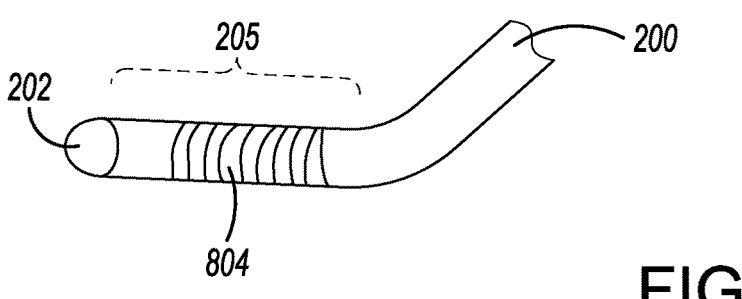

Referring to the embodiment as depicted in FIG. 7D, the elongated guidewire assembly 200 includes a compressed coil 804 mounted to the distal segment 205 of the elongated guidewire assembly 200. The compressed coil 804 is configured to be protruded from the distal portion of the elongated introducer assembly 100. The compressed coil 804 includes a radiopaque material fixed to the distal segment 205 configured to be protruded from the distal end of the elongated introducer assembly 100. Alternatively, the radiopaque material is fixed to the distal segment 205 configured to be protruded from the distal end of the elongated introducer assembly 100. The compressed coil 804 and the radiopaque material are configured to be detectable by a medical imaging system. The compressed coil 804 and the radiopaque material are configured to enable the user to visually see, via the medical imaging system (such as, under fluoroscopy or x-ray) when the distal segment 205 (that is, a required or desired length of the distal segment 205 of the elongated guidewire assembly 200) has been protruded from the distal portion of the elongated introducer assembly 100.

Figure 7E:
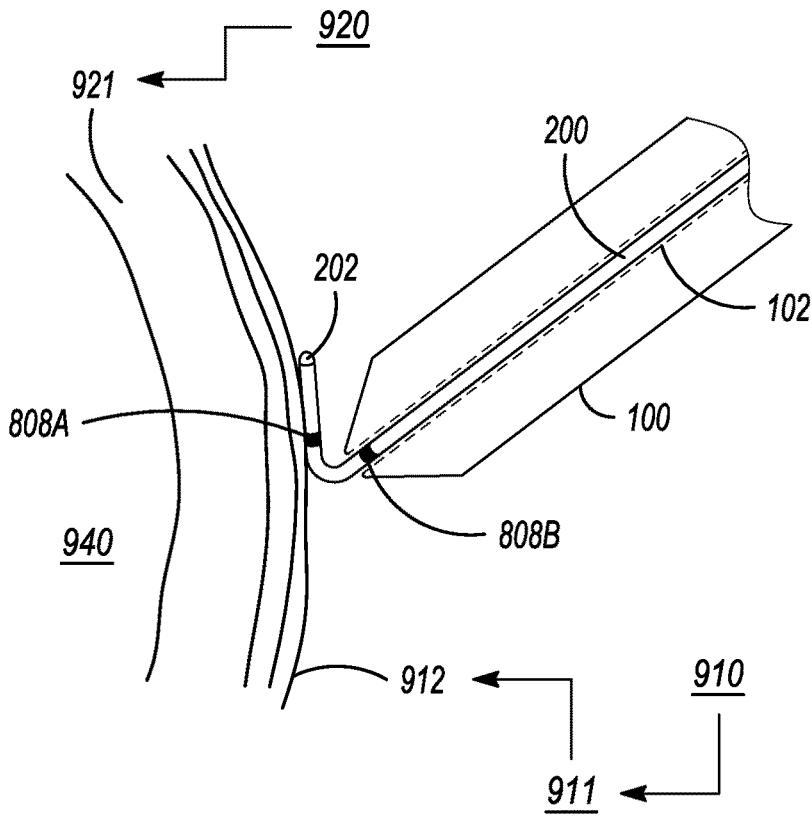

Referring to the embodiment as depicted in FIG. 7E, the elongated guidewire assembly 200 includes a first radiopaque marker 808A mounted to the distal segment 205 of the elongated guidewire assembly 200. A second radiopaque marker 808B is positioned proximate to the first radiopaque marker 808A on the elongated guidewire assembly 200. The first radiopaque marker 808A and the second radiopaque marker 808B are configured to be detectable by a medical imaging system. The first radiopaque marker 808A and the second radiopaque marker 808B are configured to enable the user to visually see, via the medical imaging system (such as, under fluoroscopy or x-ray) when the distal segment 205 (that is, a required or desired length of the distal segment 205 of the elongated guidewire assembly 200) has been protruded from the distal portion of the elongated introducer assembly 100.

Figure 7F:
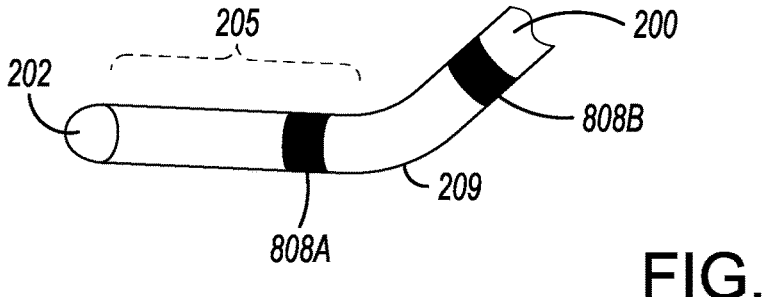

Referring to the embodiment as depicted in FIG. 7F, the elongated guidewire assembly 200 includes an elbow portion 209 configured be positioned at the distal introducer exit portal 104 after the distal segment 205 has been extended from the interior of the elongated introducer assembly 100. A first radiopaque marker 808A is mounted to the distal segment 205 of the elongated guidewire assembly 200; this is done in such a way that the first radiopaque marker 808A becomes extended from the interior of the elongated introducer assembly 100 after the distal segment 205 has been extended from the interior of the elongated introducer assembly 100. For instance, the first radiopaque marker 808A may be positioned proximate to the distal puncture device 202. A second radiopaque marker 808B is mounted to the distal segment 205; this is done in such a way that the second radiopaque marker 808B remains within the interior of the elongated introducer assembly 100 after the distal segment 205 has been extended from the interior of the elongated introducer assembly 100. For instance, the second radiopaque marker 808B may be positioned proximate to the elbow portion 209. The first radiopaque marker 808A and the second radiopaque marker 808B are configured to be detectable by a medical imaging system. The first radiopaque marker 808A and the second radiopaque marker 808B are configured to enable the user to visually see, via the medical imaging system (such as, under fluoroscopy or x-ray) when the distal segment 205 (that is, a required or desired length of the distal segment 205 of the elongated guidewire assembly 200) has been protruded from the distal portion of the elongated introducer assembly 100. The spaced-apart radiopaque markers (808A, 808B) may be used for depth measurements. The spaced-apart radiopaque markers (808A, 808B) may be placed at strategic sections on the elongated guidewire assembly 200. The spaced-apart radiopaque markers (808A, 808B) may provide feedback to the user regarding how much of the elongated guidewire assembly 200 is protruding from the distal tip of the elongated introducer assembly 100. For example, the spaced-apart radiopaque markers (808A, 808B) may be placed in about ten (10) millimeter intervals relative to the distal tip of the elongated guidewire assembly 200, thereby providing feedback about how much of the elongated guidewire assembly 200 is protruding when viewed under fluoroscopy or x-ray.

Figure 7G:
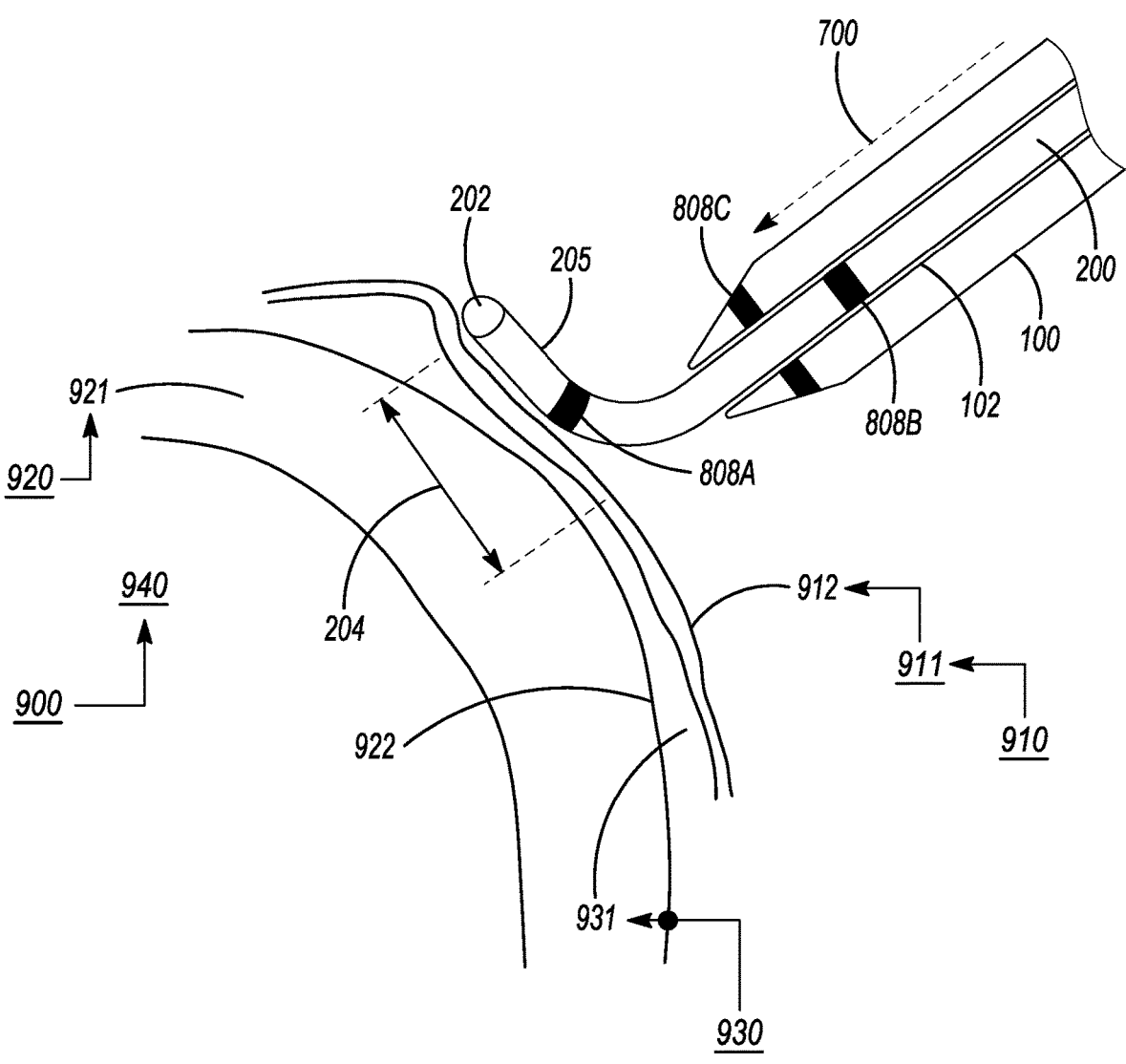

Referring to the embodiment as depicted in FIG. 7G, A radiopaque marker 808C may also be embedded within the elongated introducer assembly at its distal end (see FIG. 7G). When viewed by a medical imaging system, a user is then able to align the radiopaque marker on the elongated introducer assembly 100 between the two radiopaque markers (808A and 808B) on the elongated guidewire assembly 200 to ensure an optimal length 204 of the distal segment 205 of the elongated guidewire assembly 200 is prolapsing for an optimal application of tenting force to the first biological wall 912

Referring to the embodiments as depicted in FIG. 7A to FIG. 7G, a coil may include a radiopaque material fixed to the distal section of the elongated guidewire assembly 200. The coil may have areas of tight and loose coil windings. The pattern of the coil windings may visually create a disruption in radiopacity when viewed under medical imaging such as fluoroscopy or x-ray. For instance, an indicator to the user for the ideal protrusion length of the distal portion of the elongated guidewire assembly 200 (from the distal tip of the elongated introducer assembly 100) may be a coil stretched to create two distinct sections of tight winding. The first distal section with a tight coil winding may indicate the ideal length of the distal segment 205 (of the elongated guidewire assembly 200) to be extended from the distal portion of the elongated introducer assembly 100 while the stretched coil section may indicate where the user may need to draw (retract) the elongated guidewire assembly 200 into the elongated introducer assembly 100.

Figure 8A:
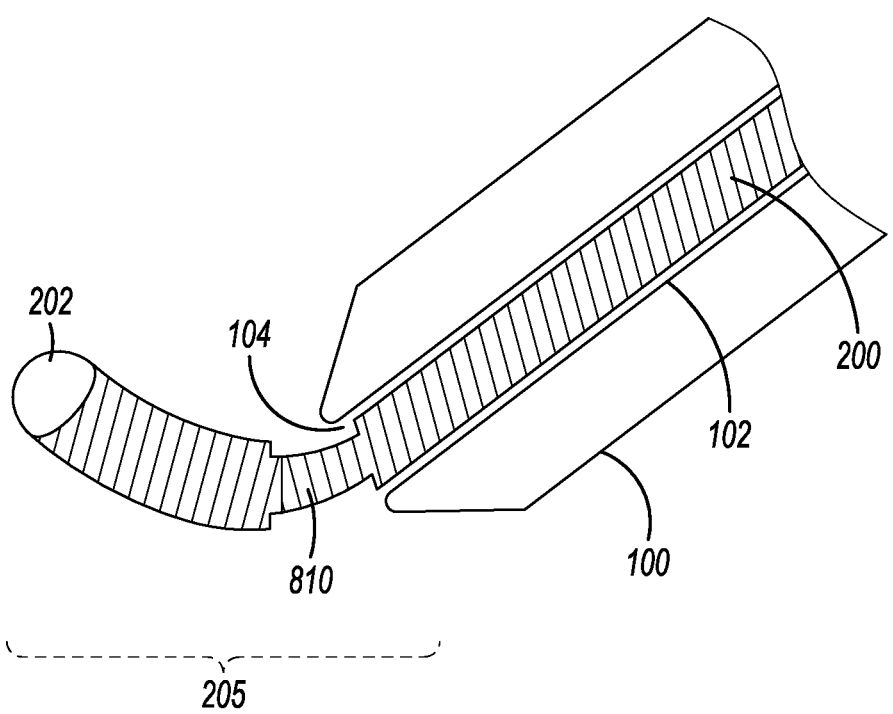
FIG. 8A, FIG. 8B and FIG. 8C depict cross-sectional views of embodiments of the elongated guidewire assembly of FIG. 3A.
Figure 8B:
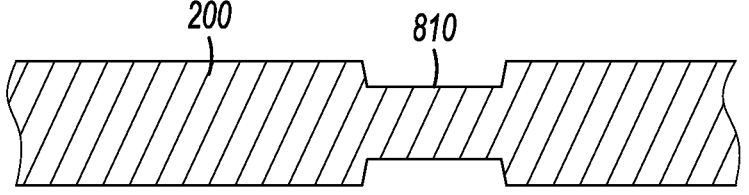
Figure 8C:
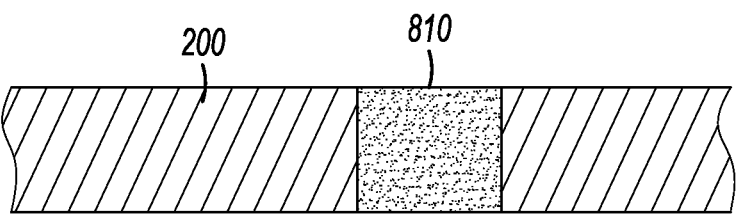

FIG. 8A, FIG. 8B and FIG. 8C depict cross-sectional views of embodiments of the elongated guidewire assembly 200 of FIG. 3A. FIG. 8A, FIG. 8B and FIG. 8C depict the embodiments associated with step (2) option (B).

Referring to the embodiment as depicted in FIG. 8A, the elongated guidewire assembly 200 includes a tactile portion 810 positioned on the distal segment 205 of the elongated guidewire assembly 200; this is done in such a way that the tactile portion 810 becomes extended from the interior of the elongated introducer assembly 100 after the distal segment 205 has been extended, at least in part, from the interior of the elongated introducer assembly 100. The tactile portion 810 is configured to provide tactile feedback to the user touching the elongated guidewire assembly 200 indicating, to the user, that the elongated guidewire assembly 200 has reached an optimal amount of protrusion of the distal segment 205 from the distal tip of the elongated introducer assembly 100. The tactile portion 810 is positioned on the distal segment 205 of the elongated guidewire assembly 200. The tactile portion 810 is positioned (on the length of the distal segment 205 of the elongated guidewire assembly 200); this is done in such a way that the tactile portion 810 becomes exposed (that is, positioned exteriorly from the elongated introducer assembly 100) after the length of the distal segment 205 of the elongated guidewire assembly 200 has been extended away from the interior of the elongated introducer assembly 100.

Referring to the embodiments as depicted in FIG. 8B and FIG. 8C, the tactile portion 810 may be placed at a guidewire proximal section of the elongated guidewire assembly 200 (the guidewire proximal section extends exterior from a proximal end of the elongated introducer assembly 100). The tactile portion 810 may be placed at the distal segment 205 of the elongated guidewire assembly 200. In accordance with an option, the tactile portion 810 may be placed at the proximal section and the distal section of the elongated guidewire assembly 200 (if so desired). The tactile portion 810 may include any tactile indicator configured to differentiate one section of the elongated guidewire assembly 200 from another section of the elongated guidewire assembly 200 based on tactile feel (for the user). The tactile portion 810 is configured to the user with tactile feedback that they have reached an optimal amount of protrusion of the elongated guidewire assembly 200 from the distal tip of the elongated introducer assembly 100. The tactile portion 810 may include a sudden change in the outer diameter of at least one section of the elongated guidewire assembly 200 that may be felt by the hand of the user (or as the distal portion of the elongated introducer assembly 100 might interact therewith). The tactile portion 810 may include knurling and/or grooves formed in the outer surface of the elongated guidewire assembly 200, or other types of indentations and/or raised sections that feel distinct from the rest of the elongated guidewire assembly 200.

Figure 9:
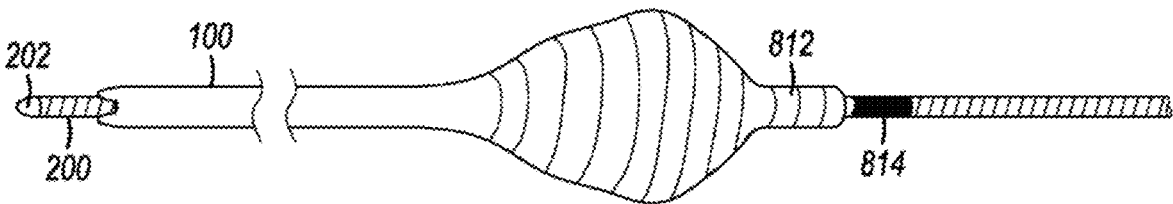
FIG. 9 depicts a side view of an embodiment of the elongated guidewire assembly of FIG. 3A.

FIG. 9 depicts a side view of an embodiment of the elongated guidewire assembly 200 of FIG. 3A. FIG. 9 depicts the embodiments associated with step (2) option (C).

Referring to the embodiment as depicted in FIG. 9, the elongated guidewire assembly 200 includes a proximal visual marker 814 positioned at a proximal end of the elongated guidewire assembly 200. The elongated introducer assembly 100 includes a hub 812. The proximal visual marker 814 of the elongated guidewire assembly 200 is configured to extend away from the hub 812 of the elongated introducer assembly 100 in such a way that the proximal visual marker 814 becomes exposed and may be visually detected by the user (in response to movement of the elongated guidewire assembly 200 proximally away from the hub 812). The proximal visual marker 814 is visually distinct from the rest of the elongated guidewire assembly 200. The proximal visual marker 814 is configured to visually indicate when an optimal length of the elongated guidewire assembly 200 is protruding from the distal tip of the elongated introducer assembly 100.

Figure 10:
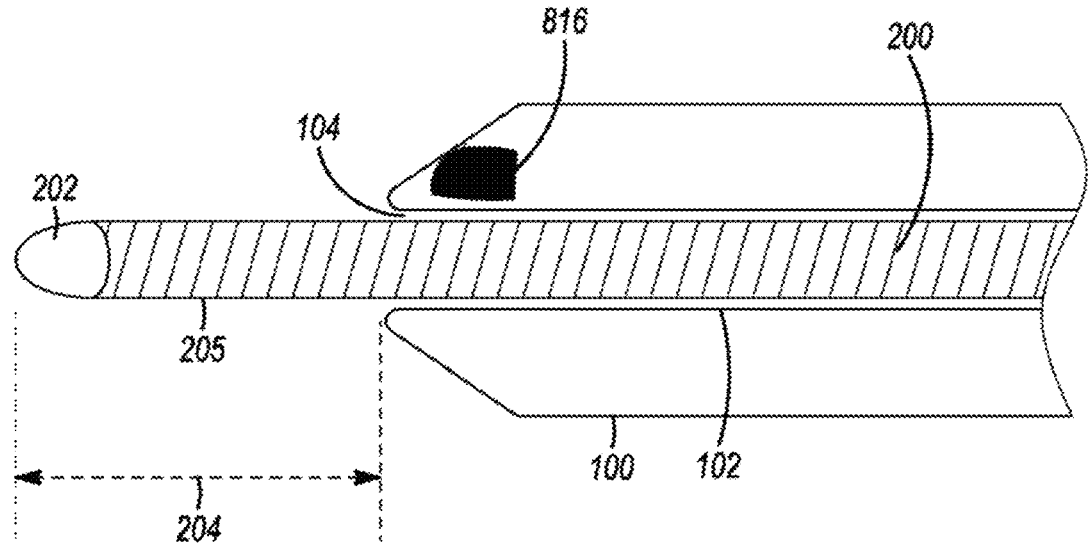
FIG. 10 depicts a cross-sectional view of an embodiment of the elongated guidewire assembly of FIG. 3A.

FIG. 10 depicts a cross-sectional view of an embodiment of the elongated guidewire assembly 200 of FIG. 3A. FIG. 10 depicts the embodiments associated with step (2) option (D).

Referring to the embodiments as depicted in FIG. 10, an optimal amount of the distal length 204 is the length (of the distal segment 205 of the elongated guidewire assembly 200) that extends from the distal introducer exit portal 104. The optimal amount of the distal length 204 is configured to transmit a desired amount of the tenting force 700 (as depicted in FIG. 3) to be applied from the optimal amount of the distal length 204 (of the distal segment 205 of the elongated guidewire assembly 200) to the first biological wall 910 (or the pericardium layer 911), as depicted in FIG. 3A. The elongated introducer assembly 100 includes a sensor 816 (such as a capacitive sensor) positioned at the distal introducer exit portal 104 of the elongated introducer assembly 100. The sensor 816 is configured to provide an indication signal indicating that the optimal amount of the distal length 204, of the distal segment 205 of the elongated guidewire assembly 200, protrudes from the distal tip of the elongated introducer assembly 100. For instance, a capacitive sensor is configured to generate an electric field and determine whether the field has been disrupted. The capacitive sensor positioned at the distal section of the elongated introducer assembly 100 may be optimized to show when the distal puncture device 202 (of the elongated guidewire assembly 200) has become extended by a critical distance (length) from the distal introducer exit portal 104 (of the elongated introducer assembly 100). This arrangement permits the user to make a determination of when the distal section of the elongated guidewire assembly 200 has become extended (protruded) a sufficient distance from the distal portion of the elongated introducer assembly 100.

Figure 11A:
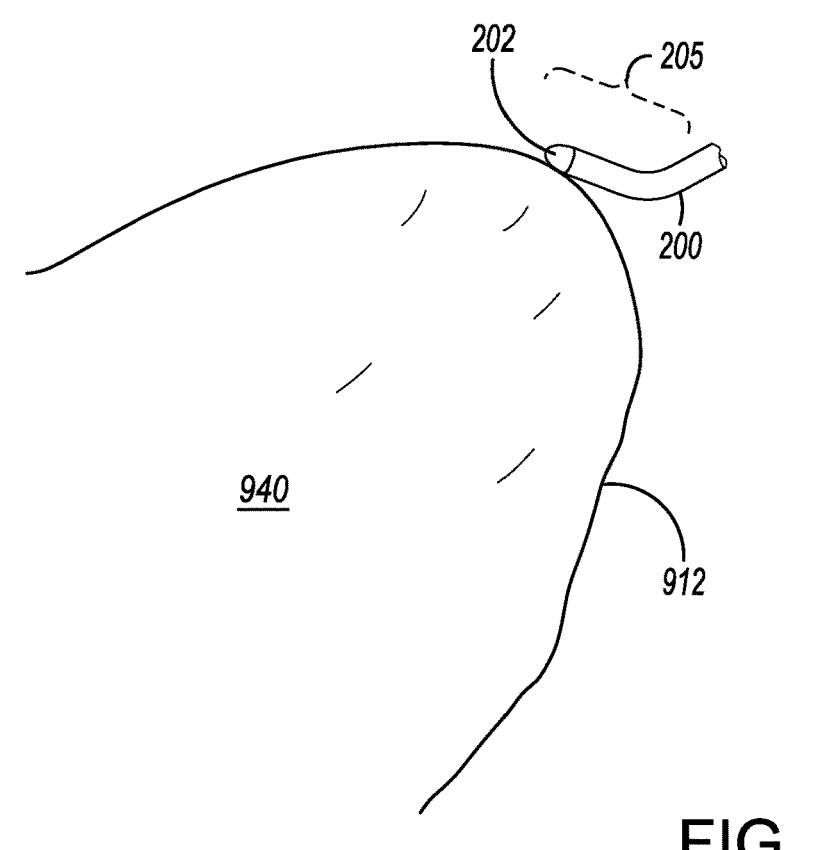
FIG. 11A and FIG. 11B depict schematic views of embodiments of the elongated guidewire assembly of FIG. 3A.
Figure 11B:
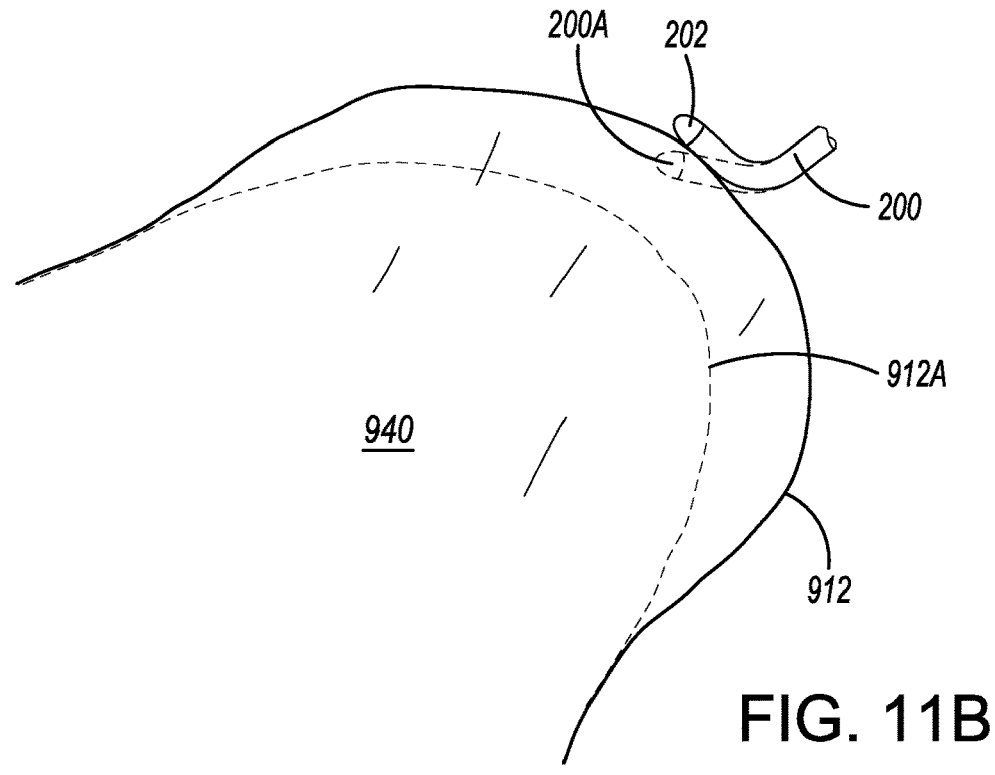

FIG. 11A and FIG. 11B depict schematic views of embodiments of the elongated guidewire assembly 200 of FIG. 3A. FIG. 11A and FIG. 11B depict the embodiments associated with step (3) option (A).

Referring to the embodiments as depicted in FIG. 11A and FIG. 11B, the heart 940 is positioned in a contracted state or systole (as depicted in FIG. 11A) and a relaxed state or diastole (as depicted in FIG. 11B). The first outer surface 912A (depicted in FIG. 11B) is positioned during the relaxed state of the heart 940. The elongated guidewire assembly 200A (depicted in FIG. 11B) is positioned during the relaxed state of the heart 940. The heart 940 moves the distal puncture device 202 (of the elongated guidewire assembly 200) in response to the beating of the heart 940. The distal puncture device 202 (of the elongated guidewire assembly 200) is positioned in contact with the first outer surface 912 (of the pericardium layer 911 of the heart). Once in contact with the heart 940, the distal puncture device 202 may move synchronously with the beating of the heart 940. This cooperative action may be visualized on a medical imaging system (such as a fluoroscopy system or an x-ray system). The user is able to view the synchronous movement of the distal puncture device 202 with the cardiac motion (of the heart 940) from a display of a medical imaging system in order to discern whether they (that is, the distal puncture device 202 and the heart 940) are in contact with each other, and therefore the user may be in a good position to proceed with puncturing the first outer surface 912 (of the pericardium layer of the heart 940).

Referring to the embodiments as depicted in FIG. 11A and FIG. 11B, observation of the distal segment 205 via a medical imaging system (such as an x-ray machine, etc.) may be utilized to detect the movement behavior of the distal segment 205 of the elongated guidewire assembly 200 for the case where the distal segment 205 s positioned proximate to a biological feature such as the heart. Prior to reaching the heart, the distal segment 205 of the elongated guidewire assembly 200 tends to be stable, whereas once or after the distal segment 205 rests on the first outer surface 912 of the first biological wall 910 (or the pericardium layer 911), the distal segment 205 may have a tendency to move along with the motions (beating) of the heart. This observed condition (observed via a medical imaging system, such as an x-ray machine) may be used to confirm that the distal segment 205 may have reached the first outer surface 912 of the first biological wall 910, as a way to confirm the a reasonable contact is established between t the distal segment 205 and the first outer surface 912 of the first biological wall 910.

Without reference to any drawings, it will be appreciated that step (3) option (B), which is not depicted, includes sensing the tenting force to be transmitted to the heart. A force contact sensing device (not depicted) is positioned at (on) a distal portion of the elongated guidewire assembly 200 (preferably, at the length to be extended from the distal portion of the elongated introducer assembly 100). The force contact sensing device is configured to provide a signal indicating whether physical contact has been made between the distal portion of the elongated guidewire assembly 200 and the first outer surface 912 (of the pericardium layer of the heart 940).

Without reference to any drawings, it will be appreciated that step (3) option (C), which is not depicted, includes setting the stiffness of the protruded section of the elongated guidewire assembly 200, preferably exceeding a critical myocardium puncture threshold. The stiffness of the distal section of the elongated guidewire assembly 200 (which is to be protruded or extended from the distal section of the elongated introducer assembly 100) may be modulated to ensure that there is insufficient tenting force for the distal puncture device 202 to puncture through the second outer surface 922 of the second biological wall 920 (such as the myocardium layer 921). There may not be a position, therefore, that the distal puncture device 202 (of the elongated guidewire assembly 200) might be placed at the set protrusion length (as depicted in FIG. 10) of the distal portion of the elongated guidewire assembly 200 that might provide stiffness (of the optimized length of the distal segment 205 as depicted in FIG. 10) that might puncture through the second outer surface 922 of the second biological wall 920 (or the myocardium layer 921), so that only puncture of the first biological wall 910 (or the pericardium layer 911) might occur. Further, with a lower stiffness of the length of the distal segment 205 (of the elongated guidewire assembly 200), the elongated guidewire assembly 200 might be less likely to puncture through; for instance, burn marks may become formed on the second biological wall 920 (or the myocardium layer 921) that might be formed during emission of radiofrequency energy emitted from the distal puncture device 202 after the elongated guidewire assembly 200 is advanced into the biological space 930 (or the pericardium space 931).

Figure 12A:
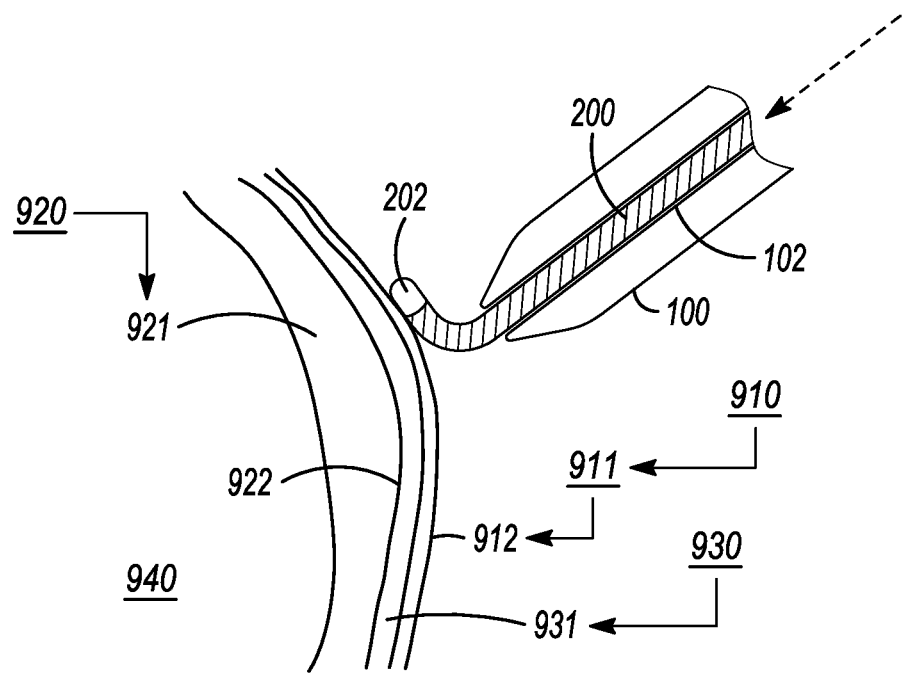
FIG. 12A and FIG. 12B depict a cross-sectional view (FIG. 12A) and a schematic view (FIG. 12B) of embodiments of the elongated guidewire assembly of FIG. 3A.
Figure 12B:
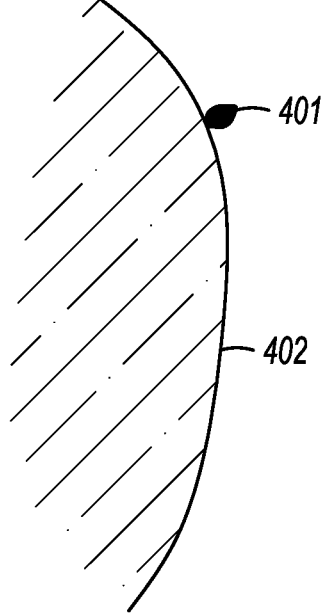

FIG. 12A and FIG. 12B depict a cross-sectional view (FIG. 12A) and a schematic view (FIG. 12B) of embodiments of the elongated guidewire assembly 200 of FIG. 3A.

Referring to FIG. 12A and FIG. 12B, there are depicted the embodiments associated with step (3) option (D).

Referring to the embodiment as depicted in FIG. 12A, the distal puncture device 202 is positioned to contact the heart 940 and is able to be visualized on the system display of a medical imaging system.

Referring to the embodiment as depicted in FIG. 12B, there is depicted the visualization of the distal puncture device 202 (of the elongated guidewire assembly 200) at a display of the electroanatomic mapping system. The first medical image 401 is associated with the distal puncture device 202 of FIG. 12A. The second medical image 402 is associated with the heart 940 of FIG. 12A. The electroanatomic mapping system enables a user to map the three-dimensional anatomy of the heart 940. The electroanatomic mapping system is configured to track the location of the elongated guidewire assembly 200 (provided that the elongated guidewire assembly 200 is placed in electrical communication with the electroanatomic mapping system). For the case where the distal puncture device 202 is configured to selectively emit energy (radiofrequency energy), the electroanatomic mapping system may provide a visual indication of the position of the distal puncture device 202 that may allow the user to determine whether there is contact between the distal puncture device 202 and the heart (as indicated in FIG. 12B).

Without reference to any drawings, it will be appreciated that step (3) option (E) includes usage of an electrogram system (EGM) to confirm contact. The electrogram system is configured to measure the electrical potential in a tissue. For the case where the distal puncture device 202 is configured to emit energy (radiofrequency energy) with a material at the distal section (of the elongated guidewire assembly 200) that is suitable for conducting electrical signals and that is able to be connected with the electrogram system; the status of the conducting electrical signals may provide feedback (to the user) indicating whether (or not) the distal puncture device 202 is in contact with the heart 940. Contact creates local ischemia that manifests as ST-segment elevation on the electrical signal. Using this relationship may help to confirm contact between the distal puncture device 202 and the heart.

Figure 13:
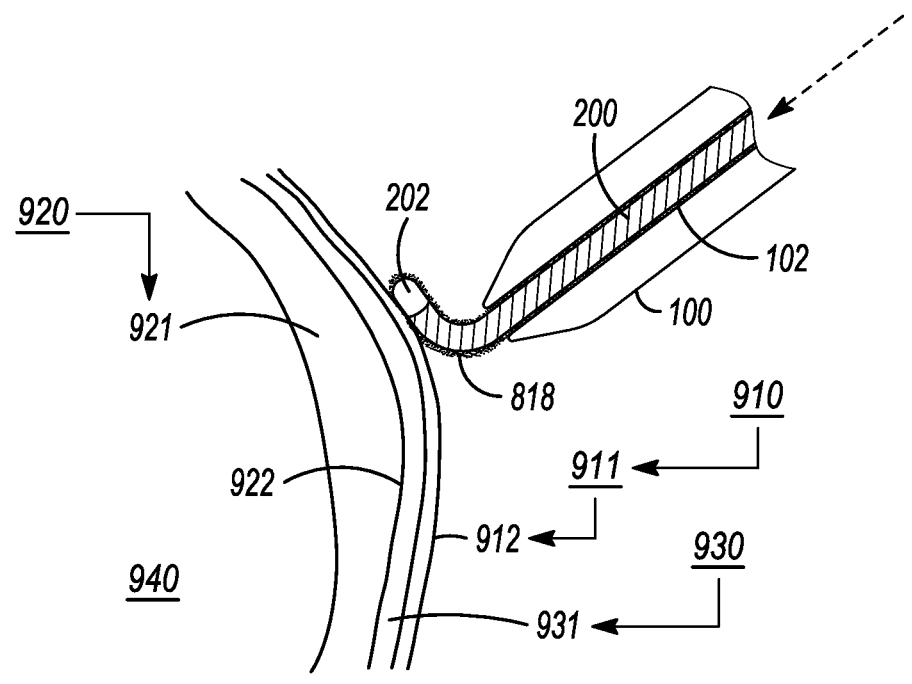
FIG. 13 depicts a cross-sectional view of an embodiment of the elongated guidewire assembly of FIG. 3A.

FIG. 13 depicts a cross-sectional view of an embodiment of the elongated guidewire assembly 200 of FIG. 3A. FIG. 13 depicts the embodiment associated with step (3) option (F).

Referring to the embodiment as depicted in FIG. 13, a contrast material 818 is injectable along the introducer lumen 102 of the elongated introducer assembly 100, flows therethrough and out from the distal introducer exit portal 104. The contrast material 818 is detectable by a medical imaging system; this is done in such a way that the contrast material 818 causes the medical imaging system to create a visual effect to be displayed for determination of whether the distal puncture device 202 is in contact with the heart 940. The contrast material 818 is configured to create a greater visual effect for the user to determine whether the distal puncture device 202 is in contact with the heart 940. The contrast material 818 may be injected through the introducer lumen 102 with the distal puncture device 202 positioned accordingly. The contrast material 818 is able to highlight surfaces and contours on a display of a fluoroscopy system or x-ray imaging system, and thereby provide (at least in part) improved image outlines of the cardiac silhouette (of the heart 940). More specifically, the region of the heart 940 where the distal introducer exit portal 104 (of the elongated introducer assembly 100) and the distal segment 205 (of the elongated guidewire assembly 200) are positioned in the vicinity of the contrast material 818; the medical imaging display may show a darkened section associated with the contrast material 818. Thereby, this arrangement makes it easier to visualize (to the user) and determine whether the distal puncture device 202 and the heart 940 might be in contact with each other.

Figure 14:
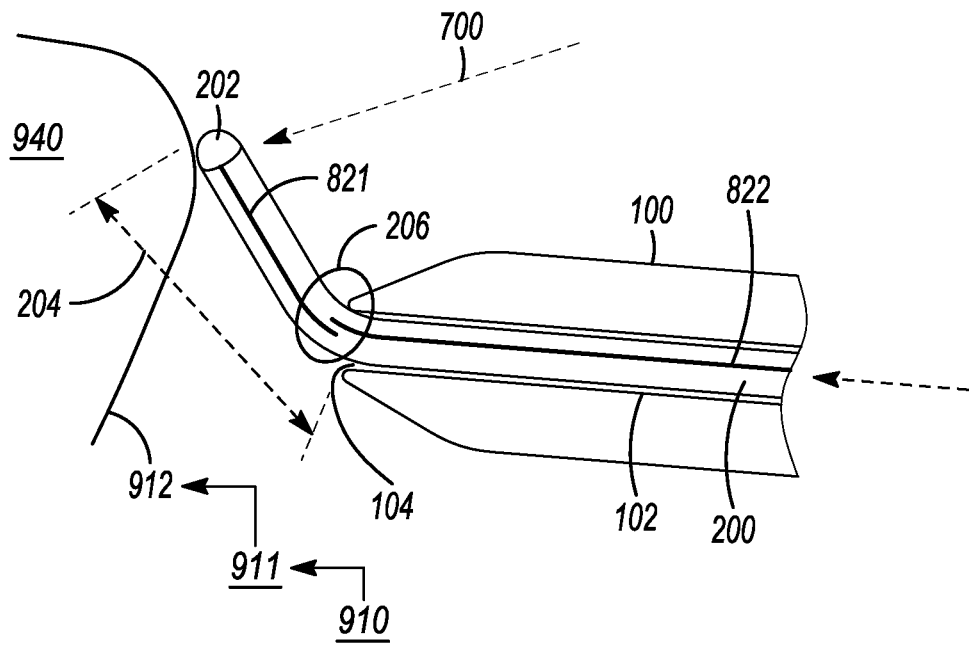
FIG. 14 depicts a cross-sectional view of an embodiment of the elongated guidewire assembly of FIG. 3A.

FIG. 14 depicts a cross-sectional view of an embodiment of the elongated guidewire assembly 200 of FIG. 3A. FIG. 14 depicts the embodiment associated with step (3) option (G).

Referring to the embodiment as depicted in FIG. 14, the elongated guidewire assembly 200 includes a first wire 821 and a second wire 822. The first wire 821 and the second wire 822 are configured to contact each other in response the distal length 204 becoming less than the optimum length. The first wire 821 and the second wire 822 are configured to disconnect from each other in response the distal length 204 becoming greater than the optimum length. The elongated guidewire assembly 200 includes an optimal distal portion 206 positioned at, and in contact with, the distal introducer exit portal 104 (after the optimal amount of the distal length 204 is extended from the distal introducer exit portal 104, also depicted in FIG. 10). For the case where the maximum desired amount of the tenting force 700 is reached, the first wire 821 and the second wire 822 become electrically disconnected from each other, thereby breaking the electrical circuit and stopping the delivery energy (radiofrequency energy) to the distal puncture device 202. In this way, puncturing may be formed through the first biological wall 910 (or the pericardium layer 911), and cannot be performed for the case where (A) an excessive amount of the tenting force 700 (that might inadvertently puncture the second outer surface 922 of the second biological wall 920 or the myocardium layer 921) is reached, or (B) the distal puncture device 202 bends away from the first outer surface 912 of the first biological wall 910 (or the pericardium layer 911). The first wire 821 and the second wire 822 are configured to contact each other in response the distal length 204 being less than the optimum length (that is, after the distal segment 205 of the elongated guidewire assembly 200 protrudes from the distal introducer exit portal 104 of the elongated introducer assembly 100). The first wire 821 and the second wire 822 are configured to disconnect from each other in response the distal length 204 being greater than the optimum length (that is, after the distal segment 205 of the elongated guidewire assembly 200 protrudes from the distal introducer exit portal 104 of the elongated introducer assembly 100).

Without reference to any drawings, it will be appreciated that step (3) option (H) includes positioning the distal puncture device at a region where cardiac motion perpendicular to the elongated introducer assembly 100 is minimized Minimization of this motion reduces the change in tenting force along the elongated guidewire assembly transmitted from the distal segment to the first biological wall. This reduction in tenting force change ensures more consistent and predictable puncture through the pericardial layer.

Without reference to any drawings, it will be appreciated that step (4) option (A) includes activation of radiofrequency energy for the time it takes to vaporize the pericardium, thereby optimizing the duration for application of radiofrequency energy). The radiofrequency application duration may be optimized to ensure that radiofrequency energy is only active for the time it takes to puncture through the pericardial layer.

Without reference to any drawings, it will be appreciated that step (4) option (B) includes activation of radiofrequency energy from the distal puncture device 202 for less than about 0.5 seconds. Radiofrequency activation times of less than about 0.5 seconds may minimize damage to the myocardium layer and ensure successful puncture of the pericardium layer.

Without reference to any drawings, it will be appreciated that step (4) option (C) includes turning off the emission of energy (such as radiofrequency energy) from the distal puncture device 202 in response to detection of an impedance change associated with the puncturing of the first outer surface 912 of the first biological wall 910 (or the pericardium layer 911). Real-time impedance measurements may be taken from the distal puncture device 202 (for the case where the distal puncture device 202 is configured to emit radiofrequency energy). Impedance values may change from outside of the heart 940 to inside of the pericardium space 931. When this impedance change is detected, radiofrequency energy delivery may be shut off to ensure that no further tissue puncture might occur.

Without reference to any drawings, it will be appreciated that a side-mounted distal puncture device is configured to emit energy (radiofrequency energy), and is mounted on (to) a side portion of the distal introducer exit portal 104 of the elongated introducer assembly 100.

Without reference to any drawings, it will be appreciated that the elongated guidewire assembly 200 may include a side-mounted distal puncture device is configured to emit energy (radiofrequency energy), and is mounted a side portion of the distal portion of the elongated guidewire assembly 200.

Without reference to any drawings, it will be appreciated that the elongated guidewire assembly 200 includes an elongated electrode configured to emit energy (radiofrequency energy).

FIG. 15 to FIG. 22 depict cross-sectional views of embodiments of the elongated guidewire assembly 200 of FIG. 3A.

Figure 15:
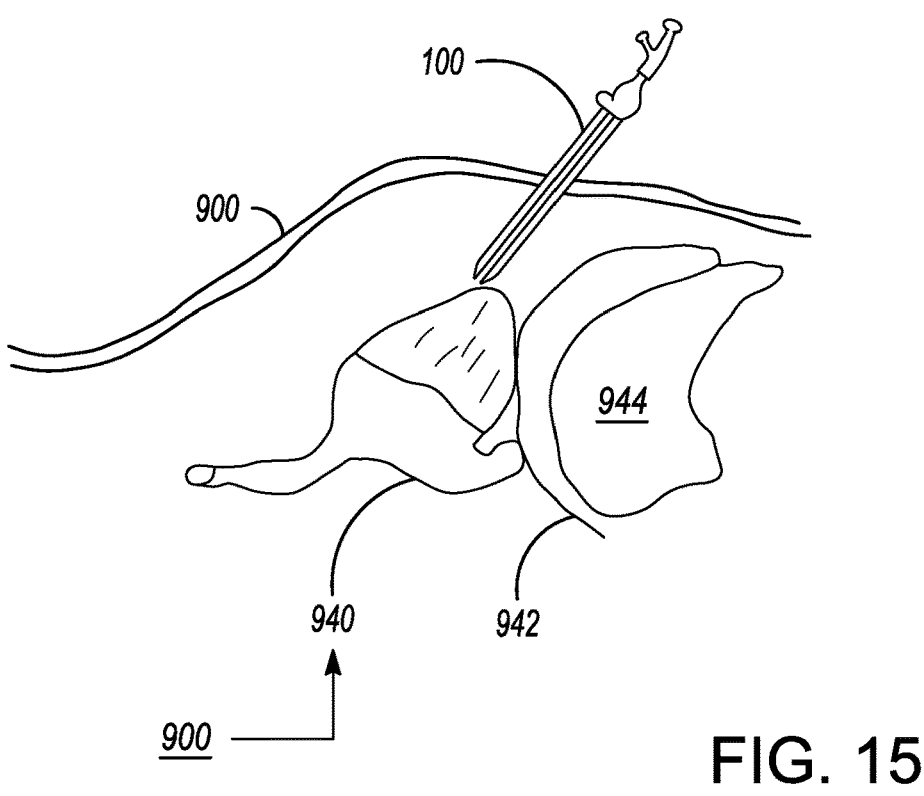
FIG. 15 to FIG. 22 depict cross-sectional views of embodiments of the elongated guidewire assembly of FIG. 3A.

Referring to the embodiment as depicted in FIG. 15, the heart 940 of the patient 900 is positioned proximate to the diaphragm 942, which is positioned proximate to the liver 944. The elongated introducer assembly 100 is installed (at least in part) into the patient 900; this is done in such a way that the distal portion of the elongated introducer assembly 100 is positioned proximate to the heart 940 of the patient 900. In this manner, percutaneous delivery of the elongated guidewire assembly 200 to the first outer surface 912 of the first biological wall 910 (or the pericardium layer 911 of the heart 940) may be accomplished via the elongated introducer assembly 100.

Figure 16:
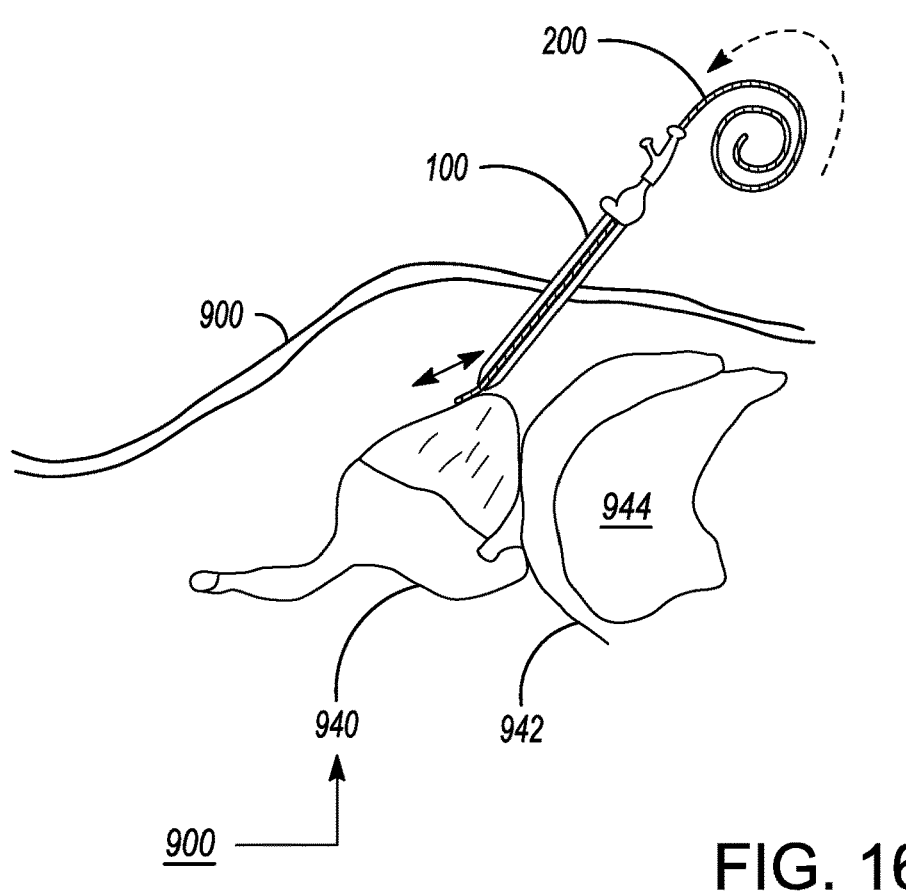

Referring to the embodiment as depicted in FIG. 16, the elongated guidewire assembly 200 is inserted into and along, and is advanced (extended) from, the elongated introducer assembly 100 (via the introducer lumen 102). This done in such a way that a length of the distal segment 205 of the elongated guidewire assembly 200 may be advanced (extended) from the distal introducer exit portal 104 of the elongated introducer assembly 100, for placement (positioning) of the distal section of the elongated guidewire assembly 200 against, or on, the first outer surface 912 of the first biological wall 910 (or the pericardium layer 911) of the heart 940.

Figure 17:
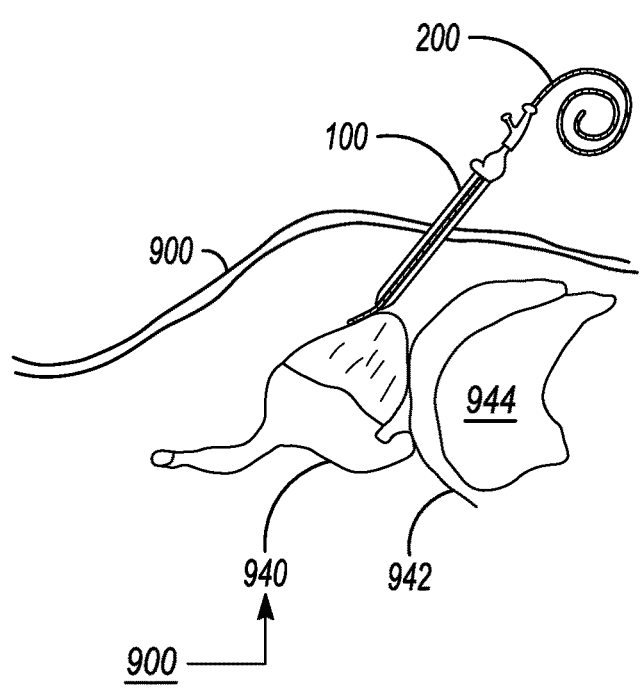

Referring to the embodiment as depicted in FIG. 17, a length of the distal segment 205 of the elongated guidewire assembly 200 is advanced (extended) from the distal introducer exit portal 104 of the elongated introducer assembly 100 (via the introducer lumen 102). This is done in such a way that the distal length 204 of the distal segment 205 of the elongated guidewire assembly 200, in use, contacts (rests on) the first outer surface 912 of the first biological wall 910 (or the pericardium layer 911) of the heart 940. The distal puncture device 202 (of the elongated guidewire assembly 200) also makes contact with the first outer surface 912 (after extending the distal section of the elongated guidewire assembly 200 from the elongated introducer assembly 100.)

Figure 18:
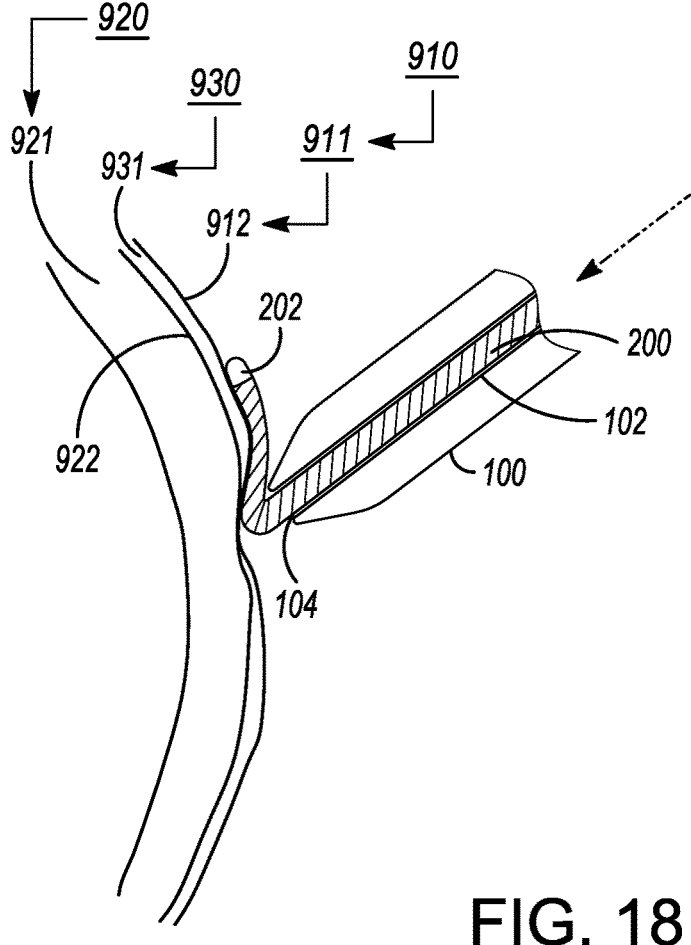

Referring to the embodiment as depicted in FIG. 18, there is depicted a close-up cross-sectional view of a length of the distal section of the elongated guidewire assembly 200 extending from the distal introducer exit portal 104 of the elongated introducer assembly 100 (via the introducer lumen 102). A distal length 204 of the distal segment 205 of the elongated guidewire assembly 200, in use, contacts (rests on) the first outer surface 912 of the first biological wall 910 (or the pericardium layer 911); advantageously, this arrangement avoids a potential (unwanted) transfer of (focusing of) the entire amount of the tenting force solely from the distal puncture device 202 (of the elongated guidewire assembly 200) toward the first outer surface 912; it will be appreciated that a focused application of the tenting force might likely, and inadvertently, impart unwanted damage to the second outer surface 922 of the second biological wall 920 or the myocardium layer 921. Advantageously, the amount of the tenting force may be dispersed over the first outer surface 912, thereby making for a relatively safer condition for puncturing through the first outer surface 912 and thereby avoiding, at least in part, imparting damage to the second outer surface 922. In this manner or arrangement, as depicted in FIG. 18, the tenting force to be applied from (by) the distal segment 205 (extending from the distal puncture device 202 of the elongated guidewire assembly 200) may be dispersed along the distal length 204 of the elongated guidewire assembly 200 that makes contact with the first outer surface 912. The tenting force to be applied at the distal length 204 of the distal segment 205 of the elongated guidewire assembly 200 (toward the first outer surface 912) remains relatively low in response to potential changes to the displacement and/or the positioning of the elongated introducer assembly 100 relative to the first outer surface 912. This arrangement gives the physician a relatively greater degree of latitude for handling the situation when attempting to impose (impart) the tenting force to the first outer surface 912 (via manipulation of the elongated guidewire assembly 200 and/or the elongated introducer assembly 100), thereby rendering a lower influence to the distal segment of the elongated guidewire assembly 200 (for the application of the tenting force to the first outer surface 912). After the distal segment 205 of the elongated guidewire assembly 200 has been extended from the distal introducer exit portal 104, and the distal length 204 of the distal segment 205 of the elongated guidewire assembly 200 has contacted the first outer surface 912, the tenting force may be applied to the distal length 204 of the distal segment 205 of the elongated guidewire assembly 200 toward the first outer surface 912, and then the distal puncture device 202 (of the elongated guidewire assembly 200) may be utilized (activated) for formation of a puncture hole through the first outer surface 912 (preferably without imparting unwanted damage to the second biological wall 920 or the myocardium layer 921).

Figure 19:
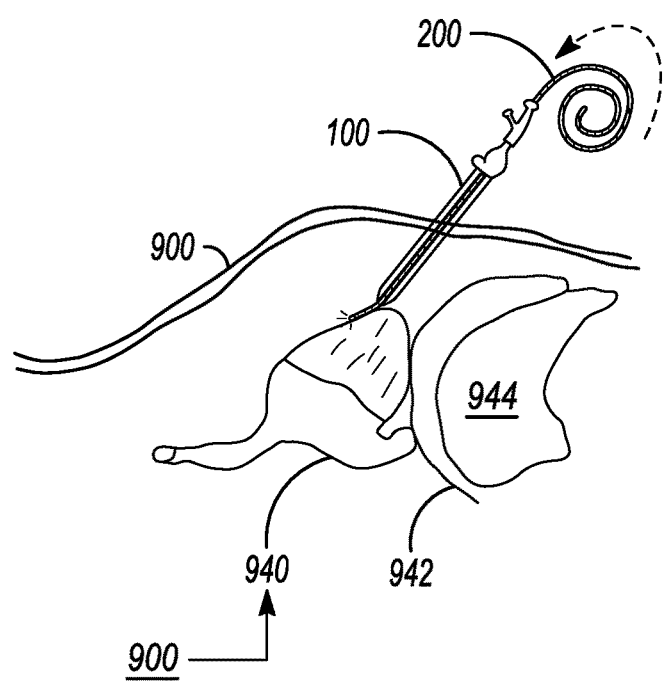

Referring to the embodiment as depicted in FIG. 19, the distal puncture device 202 (of the elongated guidewire assembly 200) is utilized for puncturing through the first biological wall 910 (or the pericardium layer 911). Preferably, the distal puncture device 202 is configured to emit energy (radiofrequency energy) to puncture through the first biological wall 910.

Referring to the embodiment as depicted in FIG. 20, after the first biological wall 910 (or the pericardium layer 911) has been punctured by the distal puncture device 202 (of the elongated guidewire assembly 200), the elongated guidewire assembly 200 is advanced into the biological space 930 (or the pericardium space 931). The direction of travel for the distal section of the elongated guidewire assembly 200 is aligned substantially parallel to the heart 940 (that is, the travel direction is aligned along the second outer surface 922 of the second biological wall 920 or the myocardium layer 921) rather than perpendicularly to the heart 940; this arrangement further reduces (at least in part) the likelihood for inadvertent puncture of the second biological wall 920 (or the myocardium layer 921).

Figures 21, 22:
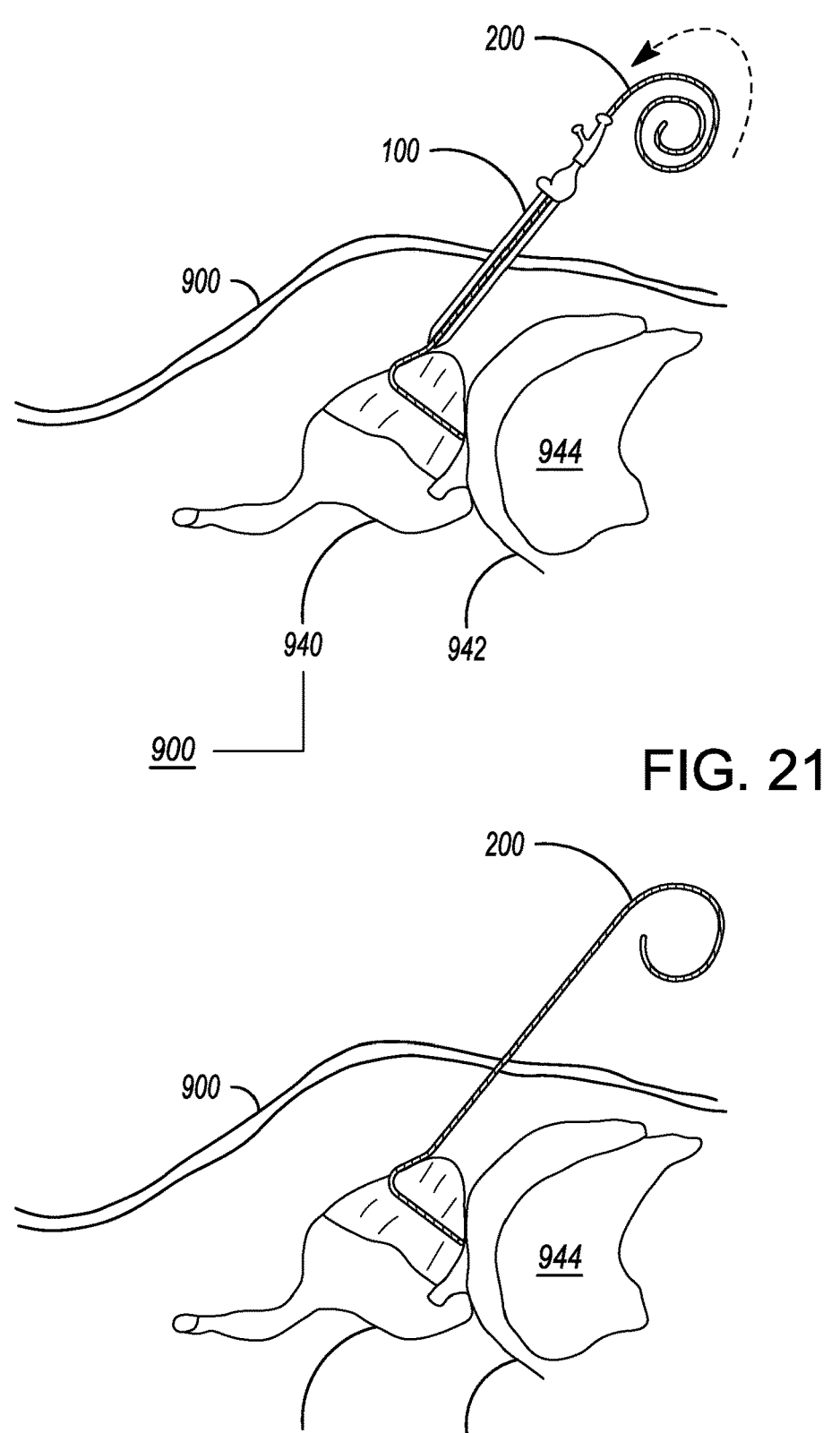

Referring to the embodiment as depicted in FIG. 21, following successful puncture (as depicted in FIG. 20) of the first biological wall 910 (or the pericardium layer 911), the distal segment of the guidewire assembly 200 is advanced into, and along, the biological space 930 (or the pericardium space 931). The distal segment of the elongated guidewire assembly 200 is advanced along a surface area of the second biological wall 920 (or the myocardium layer 921 of the heart 940), and wraps around the cardiac silhouette (of the heart 940). It will be appreciated that a portion of the distal segment of the elongated guidewire assembly 200 remains within the biological space 930 (or the pericardium space 931) while another portion of the distal segment of the elongated guidewire assembly 200 is advanced along the surface area of the second biological wall 920 (or the myocardium layer 921). In this manner, the distal segment of the elongated guidewire assembly 200 secures access (to the second biological wall 920 (or the myocardium layer 921 of the heart 940). The elongated introducer assembly 100 is then advanced toward the access site, and the elongated introducer assembly 100 is utilized for dilating the puncture hole (extending through the first biological wall 910 or the pericardium layer 911) that was created by activation (utilization) of the distal puncture device 202 of the elongated guidewire assembly 200. Dilation of the puncture hole is performed (by the elongated introducer assembly 100) to permit delivery of a known therapy device (not depicted) after the elongated introducer assembly 100 is removed from the patient 900, and the known delivery device is maneuvered along the along the guidewire assembly and is to be positioned proximate to the heart 940.

Referring to the embodiment as depicted in FIG. 22, access is secured to the second biological wall 920 (that is, access via the puncture hole formed through the first biological wall 910); preferably, the access site is dilated. The elongated introducer assembly 100 is removed (withdrawn), with the elongated guidewire assembly 200 maintaining access (to the second biological wall 920) so that the elongated guidewire assembly 200 may be utilized for delivery (deployment) of a known therapy device (as may be required). The elongated introducer assembly 100 (as depicted in FIG. 21) is fully removed (as depicted in FIG. 22) from the patient 900, and may be set aside, leaving behind the elongated guidewire assembly 200 positioned in the patient 900. The elongated guidewire assembly 200 remains, at least in part, within the patient 900, and wrapped around (at least in part) the heart 940. The distal segment of the elongated guidewire assembly 200 remains positioned proximate to the second biological wall 920 (or the myocardium layer 921) of the heart 940. A known therapy device (not depicted) may be maneuvered along the elongated guidewire assembly 200 toward the distal segment of the elongated guidewire assembly 200, through the puncture hole and past the first biological wall 910 (of the pericardium layer 911) and into the biological space 930 (or the pericardium space 931); this is done in such a way that the known therapy device may become positioned in the biological space 930 and proximate to the second biological wall 920 (or the myocardium layer 921) of the heart 940, so that the known therapy device may be utilized for delivering treatment to the second biological wall 920 of the heart 940. During deployment of the known therapy device, it is preferred that the distal puncture device 202 (of the elongated guidewire assembly 200) remains inactive (unused) while the known therapy device is deployed.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure.

The foregoing has outlined the non-limiting embodiments (examples). The description is made for particular non-limiting embodiments (examples). It is understood that the non-limiting embodiments are merely illustrative as examples.

What is claimed is:

1. A method of using an elongated guidewire assembly and an elongated introducer assembly with a first biological wall and a second biological wall, being positioned proximate to the first biological wall, of a patient, the method comprising:

selectively maneuvering the elongated guidewire assembly having a distal segment terminated at a distal puncture device along the elongated introducer assembly; and selectively protracting the distal segment and the distal puncture device away from a distal introducer exit portal after the distal introducer exit portal has been maneuvered proximate to a first outer surface of the first biological wall; and contacting, at least in part, the distal segment having a distal length with the first outer surface of the first biological wall after selectively protracting the distal segment and the distal puncture device away from the distal introducer exit portal; and applying a tenting force along, at least in part, the elongated guidewire assembly after, at least a portion of the distal segment is parallel to and has contacted, at least in part, the first outer surface of the first biological wall; and transmitting the tenting force without damaging the second biological wall, via the distal segment, from the elongated guidewire assembly to the first biological wall after the tenting force has been applied to the elongated guidewire assembly.

2. The method of claim 1, wherein the distal segment is deflected away from a longitudinal axis extending through the elongated introducer assembly by the first outer surface of the first biological wall in response to the distal length making contact with the first outer surface of the first biological wall.

3. The method of claim 1, further comprising utilizing the distal puncture device to puncture through the first biological wall.

4. The method of claim 3, wherein the distal puncture device is configured to selectively emit radiofrequency energy for puncturing through the first biological wall.

5. The method of claim 4, wherein the radiofrequency energy is activated for less than 0.5 seconds.

6. The method of claim 1, wherein the elongated guidewire assembly includes a stretched coil and a compressed coil mounted to the distal segment, and the method further comprises detecting, via a medical imaging system, the stretched coil and the compressed coil to determine when the distal segment has been protracted an amount from the elongated introducer assembly.

7. The method of claim 1, wherein the elongated guidewire assembly includes a first radiopaque marker and a second radiopaque marker positioned on the distal segment, and the method further comprises visually detecting, via a medical imaging system, the first radiopaque marker and the second radiopaque marker to determine a protrusion length of the distal segment.

8. The method of claim 1, further comprising injecting a contrast material along an introducer lumen of the elongated introducer assembly and out from the distal introducer exit portal, wherein the contrast material is detectable by a medical imaging system to determine whether the distal puncture device is in contact with the first biological wall.

9. The method of claim 1, wherein the first biological wall comprises a pericardium layer and the second biological wall comprises a myocardium layer of a heart of the patient.

10. The method of claim 1, wherein the elongated introducer assembly includes a sensor configured to be electrically connected with a medical-detection system, and the method further comprises receiving feedback from the medical-detection system about where the elongated introducer assembly is positioned relative to the first biological wall based on information provided by the sensor.

11. The method of claim 1, further comprising deactivating emission of radiofrequency energy from the distal puncture device in response to detection of an impedance change associated with puncturing of the first biological wall.

* * * * *